US008057454B2

(12) United States Patent
Long et al.

(10) Patent No.: US 8,057,454 B2
(45) Date of Patent: *Nov. 15, 2011

(54) SYSTEMS AND METHODS FOR HYDRATION SENSING AND MONITORING

(75) Inventors: Andrew Mark Long, Appleton, WI (US); Davis Dang Hoang Nhan, Appleton, WI (US); Sridhar Ranganathan, Suwanee, GA (US); Darold Dean Tippey, Neenah, WI (US); Andrew Thomas Baker, Norcross, GA (US); Thomas Michael Ales, III, Neenah, WI (US); Shawn Jeffery Sullivan, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 737 days.

This patent is subject to a terminal disclaimer.

(21) Appl. No.: 11/467,440

(22) Filed: Aug. 25, 2006

(65) Prior Publication Data

US 2008/0051745 A1    Feb. 28, 2008

(51) Int. Cl.
*A61F 13/20* (2006.01)

(52) U.S. Cl. .................. 604/385.26; 604/361

(58) Field of Classification Search .......... 604/317, 604/361, 385.01, 385.24–385.26; 340/603–605; 429/118, 207, 224
See application file for complete search history.

(56) References Cited

U.S. PATENT DOCUMENTS

| 3,199,095 A | 8/1965 | Ashida |
| 3,490,170 A | 1/1970 | Wolf |
| 3,530,855 A | 9/1970 | Balding |
| 4,163,449 A | 8/1979 | Regal |
| 4,347,683 A | 9/1982 | Maxim |
| 4,539,559 A | 9/1985 | Kelly et al. |
| 4,754,264 A | 6/1988 | Okada et al. |
| 4,834,733 A * | 5/1989 | Huntoon et al. ............. 604/361 |
| 4,977,906 A | 12/1990 | Di Scipio |
| 5,058,088 A * | 10/1991 | Haas et al. .................... 368/327 |
| 5,463,377 A | 10/1995 | Kronberg |
| 5,469,146 A * | 11/1995 | Gurler ........................... 340/605 |
| 5,570,082 A | 10/1996 | Mahgerefteh et al. |
| 5,796,345 A * | 8/1998 | Leventis et al. .............. 340/604 |

(Continued)

FOREIGN PATENT DOCUMENTS

GB    2219679    12/1989

(Continued)

OTHER PUBLICATIONS

PCT International Search Report and Written Opinion dated Jan. 4, 2008 for International Application No. PCT/US2007/076553.

(Continued)

*Primary Examiner* — Tatyana Zalukaeva
*Assistant Examiner* — Benedict L Hanrahan
(74) *Attorney, Agent, or Firm* — Armstrong Teasdale LLP

(57) ABSTRACT

Embodiments of the invention provide methods and systems for determining hydration of an article and/or a person. The physical and/or electrical properties of a device in the absorbent article may be altered by hydration received in the absorbent article. The alteration of the physical or electrical properties may indicate the amount of hydration in the absorbent article. Furthermore, a time period for receiving the hydration in the absorbent article may also be determined. The hydration of the person may be determined based on a fluid output rate from the person computed using the amount of hydration output from the person and the time period for receiving the hydration.

9 Claims, 21 Drawing Sheets

U.S. PATENT DOCUMENTS

| | | | |
|---|---|---|---|
| 5,959,535 A | 9/1999 | Remsburg | |
| 5,978,712 A | 11/1999 | Suda et al. | |
| 6,093,869 A | 7/2000 | Roe et al. | |
| 6,097,297 A | 8/2000 | Fard | |
| 6,313,646 B1 | 11/2001 | Davis et al. | |
| 6,384,296 B1 | 5/2002 | Roe et al. | |
| 6,573,837 B2 * | 6/2003 | Bluteau | 340/604 |
| 6,603,403 B2 | 8/2003 | Jeutter et al. | |
| 6,677,859 B1 | 1/2004 | Bensen | |
| 6,713,660 B1 | 3/2004 | Roe et al. | |
| 6,774,800 B2 | 8/2004 | Friedman et al. | |
| 6,870,479 B2 | 3/2005 | Gabriel | |
| 7,053,781 B1 | 5/2006 | Haire et al. | |
| 7,071,830 B2 | 7/2006 | Sahlberg et al. | |
| 7,280,441 B2 * | 10/2007 | MacDonald et al. | 368/327 |
| 2004/0059212 A1 | 3/2004 | Abreu | |
| 2004/0095247 A1 | 5/2004 | De Haan et al. | |
| 2004/0128153 A1 | 7/2004 | Zhang et al. | |
| 2004/0171962 A1 | 9/2004 | Leveque et al. | |
| 2004/0242976 A1 | 12/2004 | Abreu | |
| 2005/0046578 A1 | 3/2005 | Pires | |
| 2005/0070778 A1 | 3/2005 | Lackey et al. | |
| 2005/0099294 A1 | 5/2005 | Bogner et al. | |
| 2005/0137542 A1 * | 6/2005 | Underhill et al. | 604/361 |
| 2007/0049884 A1 * | 3/2007 | Long et al. | 604/361 |
| 2007/0083174 A1 * | 4/2007 | Ales et al. | 604/361 |
| 2007/0252712 A1 * | 11/2007 | Allen et al. | 340/573.5 |
| 2008/0082062 A1 * | 4/2008 | Cohen et al. | 604/361 |
| 2008/0147030 A1 * | 6/2008 | Nhan et al. | 604/361 |
| 2008/0266117 A1 * | 10/2008 | Song et al. | 340/573.5 |
| 2009/0062757 A1 * | 3/2009 | Long et al. | 604/361 |
| 2009/0062758 A1 * | 3/2009 | Ales et al. | 604/361 |

FOREIGN PATENT DOCUMENTS

| | | |
|---|---|---|
| JP | 2002233548 | 8/2002 |
| JP | 2005000602 | 1/2005 |
| WO | 2006009404 | 1/2006 |
| WO | 2006028347 | 3/2006 |

OTHER PUBLICATIONS

Ki Bang Lee, "Urine-activated paper batteries for biosystems", Journal of Micromechanics and Microengineering, vol. 15, pp. S210-S214, Aug. 15, 2005, Institute of Physics Publishing, UK.

Shaoni Bhattacharya, "Pee-powered battery smaller than a credit card", NewScientist.com, Aug. 15, 2005.

John Roach, "Urine Battery Turns Pee Into Power", National Geographic News, http://news.nationalgeographic.com/news/2005/08/0818_050818_urinebattery.html, Aug. 18, 2005.

"Urine-powered battery developed (Update)", PhysOrg.com, http://www.physorg.com/news5805.html, Aug. 15, 2005.

Bjorn Carey, "Scientists develop pee-powered battery", LiveScience, MSNBC.com, http://www.msnbc.msn.com/id/8973626.1098.html, Aug. 16, 2005.

Lucy Sherriff, "Scientists invent pee-powered battery", The Register, http://www.theregister.com.uk/2005/08/15/pee-powered_battery.html, Aug. 15, 2005.

"Pee Power", Shallow Thoughts to Profound Insights, http://shallowthgts.blogspot.com/2005/08/pee-power.html, Aug. 24, 2005.

Non-final Office action regarding U.S. Appl. No. 11/742,448, dated Jun. 29, 2009.

Non-final Office action regarding U.S. Appl. No. 11/742,448, dated Apr. 5, 2010.

* cited by examiner

SYSTEMS AND METHODS FOR HYDRATION SENSING AND MONITORING

BACKGROUND OF THE INVENTION

1. Field of the Invention

The present invention generally relates to determining hydration in an absorbent article or a person.

2. Description of the Related Art

Determining the hydration of a person may be critical to providing proper care to persons who may not be able to care for themselves. Providing proper care may involve providing such persons with sufficient nutrition. Some of the most important nutrients are fluid, for example, water. Water plays a vital role in regulating body temperature, transporting other nutrients and oxygen to cells, removing waste, cushioning joints, protecting organs and tissues, and many other significant biological functions. Therefore, keeping a person well hydrated is vital to maintaining the health of the person.

Determining hydration may be especially critical while caring for newborns who are unable to communicate with a caregiver. For example, it is crucial for a newborn to get sufficient nutrition in the first few weeks to ensure proper development. In the case of breast-feeding babies, mothers have great difficulty in judging whether their babies are receiving sufficient milk. Typically, pediatricians advise parents to monitor the number of diapers that are wetted by the child per day or check the wetness of the child's mucosal membranes to determine whether the child is sufficiently hydrated. In other words, pediatricians rely on the excretion of bodily fluids to determine the hydration of children.

However, current methods only provide a crude estimate of the excretion of bodily fluids, which may not accurately indicate the hydration of a person. Therefore, there is a need not only to determine the amount of fluid output from a person but also a rate of fluid output, which provides a better indication of whether a person is hydrated.

Accordingly, what is needed are methods, systems, and articles of manufacture to measure the amount and the rate of fluid output from a person.

SUMMARY OF THE INVENTION

The present invention generally relates to determining hydration in an absorbent article or a person.

One embodiment of the invention provides an absorbent article comprising a device for measuring an amount of hydration in the absorbent product, the device being disposed in an absorbent area for receiving hydration in the absorbent product, wherein the hydration alters at least one of an electrical property and a physical property of the device, the altering of the property providing an indication of a plurality of degrees of an amount of hydration in the absorbent product irrespective of the number of times the absorbent product is insulted.

In one embodiment, the electrical property altered is an equivalent resistance of the device. In one embodiment, the device comprises a plurality of resistors wherein the hydration connects one or more resistors of the plurality of resistors to each other, thereby altering an equivalent resistance of the device, the equivalent resistance indicating the amount of hydration. In one embodiment the one or more resistors are connected to each other in parallel.

In one embodiment, the equivalent resistance correlates to a dimension of one or more insult areas of the absorbent article, the one or more insult areas defined by the hydration, and wherein the dimension correlates to the amount of hydration. In one embodiment, the dimension is a length of the insult area.

In one embodiment, the device comprises a ruler printed with ink on the absorbent area, wherein the hydration alters a visual characteristic of the ink in a hydrated area defined by the hydration, whereby the length of the ruler comprising the altered ink provides an indication of the amount of hydration. In one embodiment, the spacing on the ruler is adjusted according to the weight profile and shape of the incontinence product.

In one embodiment, the device comprises a first conductor and a second conductor disposed separate from one another in the absorbent area, wherein the hydration electrically connects a portion of the first conductor to a portion of the second conductor thereby altering a resistance between the first conductor and the second conductor, the resistance indicating the amount of hydration. In one embodiment, the first foil is pre-stretched foil.

In one embodiment, the first foil is interleaved between a plurality of barriers, wherein the first foil is disposed around each barrier, and the barriers are configured to prevent a first portion of the first foil from being in contact with a second portion of the first foil.

In one embodiment, the first foil strip comprises a plurality of creases, each crease creating a gap between a first portion of the first foil strip and a second portion of the first foil strip, wherein each gap forms a resistor in series with the first portion and the second portion. In one embodiment, a resistance of the gap is greater than a resistance of the first portion and the second portion. In one embodiment, the hydration may reduce the resistance of the gap.

In one embodiment, the device comprises an absorbent thread comprising a conductive material, wherein the hydration hydrates a variable length of the thread thereby altering a resistance of the thread, the resistance of the thread indicating the amount of hydration.

In one embodiment of the invention, the device comprises a wick, wherein the hydration hydrates a portion of the wick, thereby altering a resistance of the wick, the equivalent resistance indicating an amount of hydration. In one embodiment, a plurality of resistors may be connected to the wick wherein the hydration along the wetted length of the wick connects one or more of the plurality of resistors to each other, thereby altering the equivalent resistance of the device.

Another embodiment of the invention provides a method for determining hydration in an absorbent article. The method generally comprises measuring at least one of an electrical property and a physical property of a device in the absorbent product, wherein the measured property of the device is altered by the hydration, and determining an amount of hydration in the absorbent article at least in part on the basis of the property as altered by the hydration.

In one embodiment, the device comprises a resistor wherein the hydration alters the resistance of the resistor and the resistance of the resistor is associated with the equivalent resistance of the device. In one embodiment, the device comprises a plurality of resistors, wherein the hydration connects one or more resistors of the plurality of resistors to each other, thereby altering the equivalent resistance of the device.

In one embodiment, the method may further include determining the amount of hydration on the basis of the electrical property comprises associating the electrical property, as altered by the hydration, to a dimension of a wetted area of the incontinence product comprising the hydration, the dimension indicating the amount of hydration.

In one embodiment, the method may further comprise determining a time period over which the hydration is received in the incontinence product.

Yet another embodiment of the invention provides a system for measuring hydration in a person. The system generally comprises an absorbent article and a processing circuit. The absorbent article generally comprises an absorbent area for receiving the hydration, and a device disposed on the absorbent area, wherein one or more electrical properties of the device is altered by the hydration. The processing circuit may be configured to monitor the one or more electrical properties of the device, and determine the amount of hydration based on the alteration of the electrical properties.

One embodiment of the invention provides a method for determining hydration in a person, comprising determining an amount of hydration received in an absorbent product worn by the person, determining a time period over which the hydration was received in the absorbent product, and determining a rate of hydration output from the person based on the amount of hydration received in the absorbent product and the time period, wherein the rate of hydration output indicates whether the person is adequately hydrated.

One embodiment of the invention provides a system for determining hydration in a person, comprising an absorbent product comprising an absorbent area for receiving the hydration, and a device disposed on the absorbent area, wherein one or more electrical properties of the device is altered by the hydration. The system may further include a microprocessor configured to monitor the one or more electrical properties of the device, and determine the amount of hydration based on the alteration of the electrical properties, and a timer configured to determine a time period over which the hydration is received in the absorbent product.

One embodiment of the invention provides a method for manufacturing a device for measuring hydration in an incontinence product. The method generally comprises stretching a first set of barriers defined in the device away from a second set of barriers defined in the device, wherein the first set of barriers and second set of barriers are elastic and predisposed to interleave with each other, placing a foil between the first set of barriers and the second set of barriers, and releasing the first set of barriers and the second set of barriers, thereby causing the foil to form around each barrier of the first set of barriers and the second set of barriers, wherein each barrier prevents a first portion of the foil from being in contact with a second portion of the foil.

On embodiment of the invention provides a method for manufacturing a device for measuring hydration in an incontinence product. The method generally comprises placing a foil on a surface comprising a plurality of recess areas formed on the surface, creating a vacuum in an area beneath the surface comprising the foil such that, in each recess area a portion of the foil is sucked through the recess area to create a creased portion in the foil, the creased portion of the foil creating a gap between a first portion of the foil and a second portion of the foil.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Embodiments of the invention generally relate to determining hydration in an absorbent article and/or a person. The physical or electrical properties of a device in the absorbent article may be altered by hydration received in the absorbent article. The alteration of the physical or electrical properties may indicate the amount of hydration in the absorbent article.

Furthermore, a time period for receiving the hydration in the absorbent article may also be determined. The hydration of the person may be determined based on a fluid output rate from the person computed using the amount of hydration output from the person and the time period for receiving the hydration.

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, in various embodiments the invention provides numerous advantages over the prior art. However, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Exemplary System

Figure 1A:
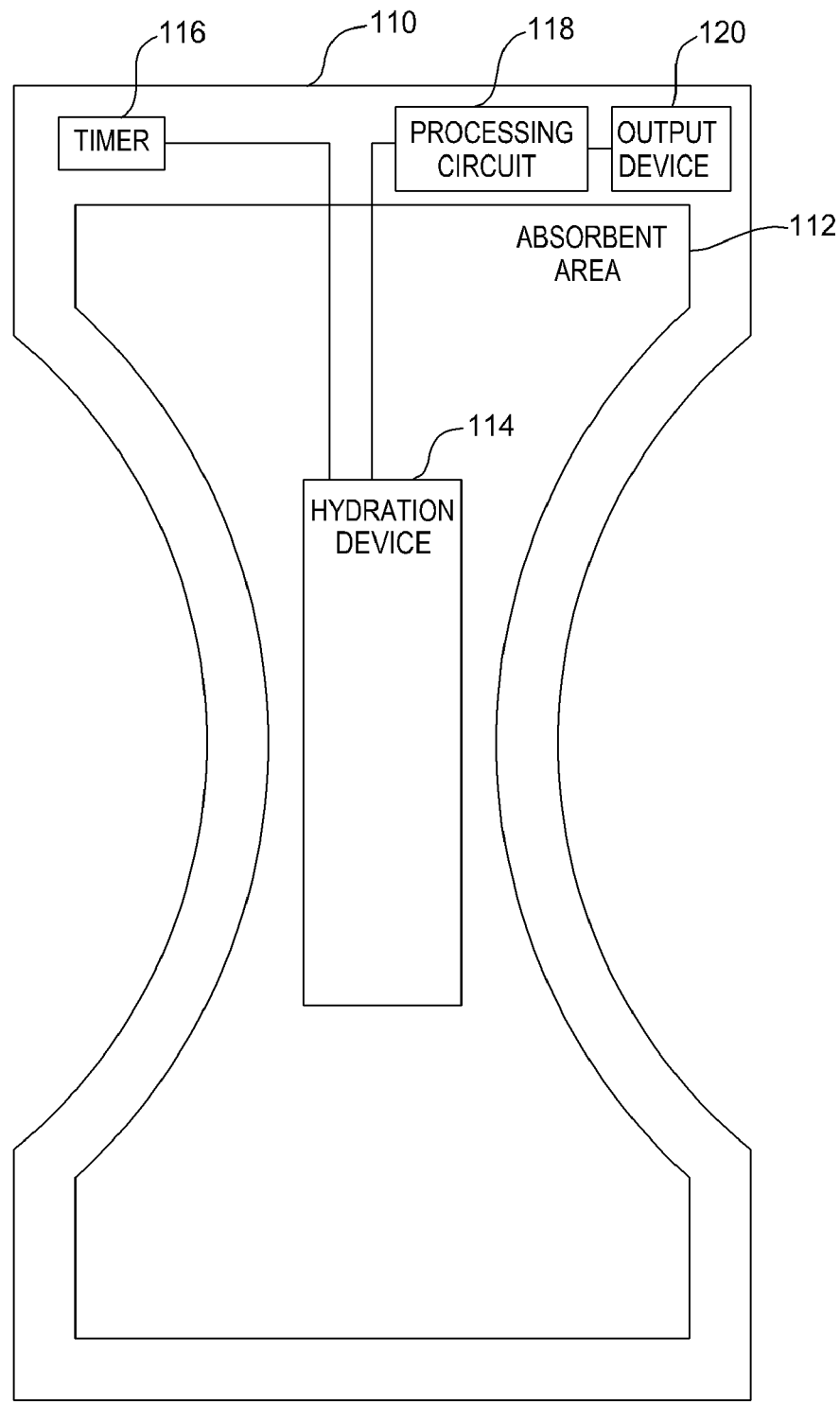
FIG. 1A is an illustration of an exemplary system according to an embodiment of the invention.

FIG. 1A is an illustration of an exemplary system 100 in which embodiments of the invention may be implemented. As illustrated, system 100 includes an absorbent article 110. Absorbent article 110 may or may not be disposable. For purposes of illustration, absorbent article 110 is shown as a diaper. However, one skilled in the art will recognize that absorbent article 110 may include any article intended for personal wear, including, but not limited to, training pants, feminine hygiene products, incontinence products, medical garments, surgical pads, bandages, personal care or health care garments, and the like. More generally, absorbent article 110 may be any article configured to receive and retain fluid.

Absorbent article 110 may include an absorbent area 112, hydration device 114, processing circuit 118, and timer 116. Absorbent area 112 may be made from any appropriate material configured to absorb and retain fluid. For example, absorbent area 112 may be made from cotton, synthetic polymers such as hydrogels, superabsorbents, hydrocolloids, absorbent web materials, and the like.

Absorbent article 110 may include a hydration device 114 disposed in the absorbent area 112. Hydration received in absorbent area 112 may alter an electrical or physical property of the device. The altering of the electrical or physical property of hydration device 114 may provide an indication of the amount of hydration received in the absorbent area. For example, hydration received in absorbent area 112 may alter an electrical property, for example, resistance, conductance, impedance, capacitance, inductance, or the like of hydration device 114. The amount of fluid in absorbent area 112 may be determined based on the change in the electrical property. Illustrative embodiments of hydration device 114 may include any combination of a resistor array device, parallel foil device, a wick-based device, and printed rulers discussed in greater detail in the following sections.

Processing circuit 118 may be coupled with hydration device 114 as illustrated in FIG. 1. Processing circuit 118 may be configured to measure an electrical or physical property of hydration device 114. For example, in one embodiment, processing circuit 118 may be configured to measure an electrical resistance of hydration device 114.

In one embodiment, an output device 120 may be coupled with absorbent article 110. Processing circuit 118 may be configured to provide output device 120 data associated with the hydration of the absorbent article 110 or a person wearing absorbent article 110. The output device may be coupled permanently or detachably with absorbent article 110.

In one embodiment of the invention, output device 120 may include a display means, for example, a Liquid Crystal Display (LCD), coupled with absorbent article 110. Processing circuit 118 may be configured to display a value indicating hydration of a person wearing the absorbent article. For example, processing circuit 118 may display any combination of the measured electrical or physical property of hydration device 114, the amount of hydration in absorbent area 112, a rate of fluid output from a person wearing absorbent article 110, and the like.

In one embodiment of the invention output device 120 may include an array of Light Emitting Diodes (LEDs) for displaying a value for indicating the hydration of the absorbent article or a person wearing the absorbent article. For example, as the absorbent article hydrated, one or more LEDs may be lit to indicate the amount of hydration in the diaper. In one embodiment, a plurality of arrays may be provided, each array depicting a value associated with the hydration of the absorbent article or a person wearing the absorbent article. For example, a first array may indicate the hydration loading of the absorbent article, a second array may depict the number of insults, a third array may indicate a hydration status of the person wearing the diaper, and so on. Each array may be differentiated for example, by the color of light emitted by the array. For example, red LEDs may depict loading, green LEDs may depict number of insults, and so on.

In one embodiment, the display means may output a qualitative description of the hydration of the absorbent article or a person wearing the absorbent article. For example, the display means may output a plurality of levels of hydration ranging from, for example, "well hydrated" to "severely dehydrated," or some equivalent scale thereof for determining hydration, thereby allowing a caregiver to take appropriate action. In one embodiment, the display means may be configured to display a suggested course of action for a caregiver based on the hydration status of the absorbent article or the person. For example, the suggested course of action may include "change diaper," "feed milk/water," and the like.

Processing circuit 118 may include logic for determining a qualitative output based on one or more parameters measured by the processing circuit. For example, in one embodiment, processing circuit may determine the qualitative output based on measurements of hydration in the absorbent article. In one embodiment, processing circuit 118 may be coupled with memory comprising data for determining the qualitative output. For example, the data may include ranges of fluid output rates, wherein each range is associated with a particular hydration recommendation for the caregiver. Processing circuit 118 may measure the fluid output rate in the absorbent article, compare the fluid output rate to the range data, and provide a qualitative output using the display means to the caregiver.

In one embodiment, processing circuit 118 may be configured to receive one or more inputs from a caregiver. A caregiver may provide, for example, age and weight profile of the wearer of the absorbent article. Processing circuit 118 may use the data inputs for calculating one or more values, for example, the fluid output rate, a recommendation for a course of action, and the like. Accordingly, one or more input devices, for example, buttons, dip switches, and the like, may be coupled with the absorbent article for facilitating data input. In one embodiment, the input device may be integrated with output device 120, for example, a touchscreen.

In one embodiment of the invention, output device 120 may include a wireless transmitter to transmit data from the absorbent article to another device, for example, a computer, cell phone, personal digital assistant, and the like. The transmitted data may include, for example, the measured electrical or physical property of hydration device 114, the amount of hydration in absorbent area 112, a rate of fluid output from a person wearing absorbent article 110, a qualitative description of the hydration status of the absorbent article or a person wearing the absorbent article, a suggested course of action, and the like.

In one embodiment, output device 120 may connect with the Internet for uploading hydration data to a website configured to accumulate and analyze hydration data. The analysis of data may include, for example, comparing received data with historic hydration data accumulated for a user of the absorbent article. The analysis may be sent to a care giver, for example, via email, text message, and the like.

In one embodiment of the invention, output device 120 may also include a receiver for receiving wireless signals from a device, for example, a computer. In one embodiment, output device 120 may transmit hydration data to one or more peripheral processing devices, for example, a computer, website, cell phone, and the like. The peripheral device may analyze the data and transmit one or more signals to the absorbent article. The transmitted signals may include data for display on the output device, for example, a recommended course of action for a caregiver. Accordingly, processing circuit 118 may be configured to display data received via the receiver on the display means.

Absorbent article 110 may also include a timer 116. Timer 116 may be configured to determine a time period over which hydration is received in absorbent article 110. For example, in one embodiment, timer 116 may be coupled with a diaper and may be configured to start at the time when hydration is first received in the diaper. The timer may be stopped at the time of removal of the diaper, thereby providing a time period over which hydration is received in the diaper. In one embodiment, timer 116 may be detachably coupled with absorbent article 110. Therefore, the same timer may be used to determine a time period for receiving hydration in multiple absorbent articles. Embodiments of the timer 116 are described in greater detail below.

Hydration Devices

To determine a rate of fluid output from a person, the amount of fluid expelled from the person must be determined. The amount of fluid expelled may be determined by the amount of fluid received in an absorbent article, for example absorbent article 110 illustrated in FIG. 1. As previously described, the amount of hydration in an absorbent article may be determined by measuring an electrical or physical property of a hydration device 114 in absorbent article 110.

Figure 1B:
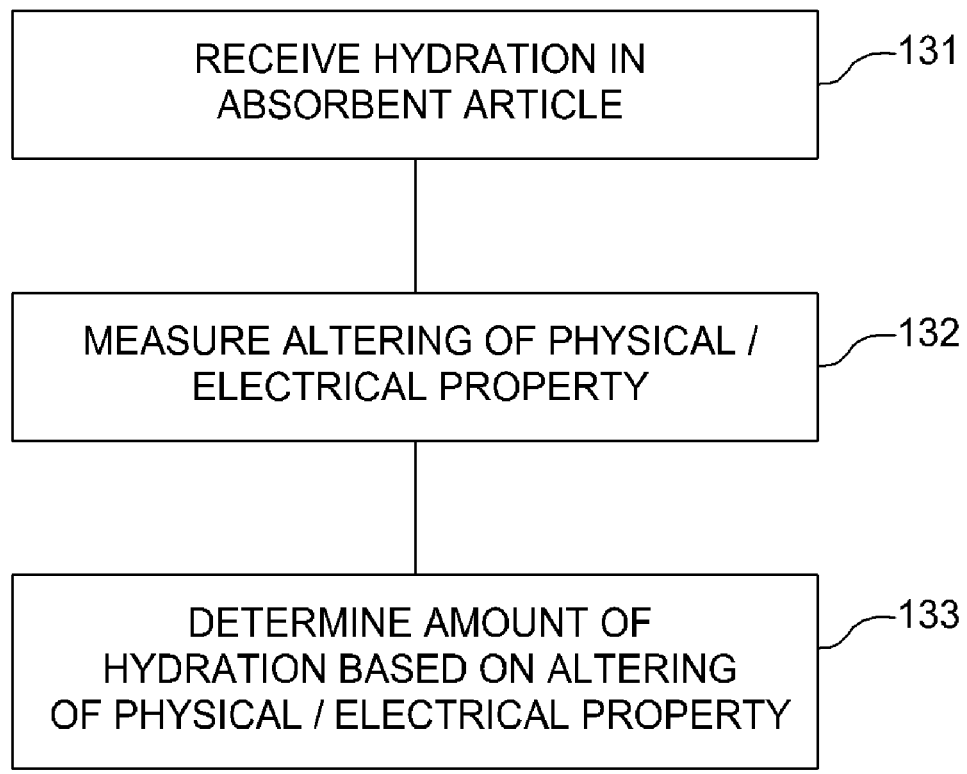
FIG. 1B is a flow diagram of exemplary operations performed to determine an amount of hydration in an absorbent article, according to an embodiment of the invention.

FIG. 1B illustrates a flow diagram of exemplary operations performed to determine the amount of hydration in absorbent area 112. The operations begin in step 130 by receiving hydration in an absorbent area 112 of an absorbent article 110. The hydration received in the absorbent area 112 may alter a physical or electrical property of a hydration device 114 disposed in the absorbent area.

In step 132, the altering of the physical or electrical property of hydration device 114 may be measured. For example, processing circuit 118 may measure a change in an equivalent resistance of the hydration device to determine the amount of hydration in the absorbent area. In step 133, the amount of hydration in the absorbent area may be determined based on the altering of the physical or electrical property of the hydration device.

In one embodiment of the invention, determining the amount of hydration in the absorbent article may involve determining a dimension of a wetted region in the absorbent area based on the altering of the physical or electrical property. The dimensions of the wetted region may include, for example, a length of the wetted region, the area of the wetted region, and the like. The dimension of the wetted region may be correlated with an amount of hydration in the absorbent area.

For example, the absorbent area may have a predefined length, width, and depth. In one embodiment, the predefined length may be 18 inches. Furthermore, based on the predefined width and depth of the absorbent area, the absorbent article may have a total capacity of 500 ml. Hydration received in the absorbent area may soak along the width of the absorbent area and wet the absorbent area for a length of, for example, 5.4 inches. The amount of hydration in the absorbent area may then be calculated as following:

$$\text{Amount of Hydration} = \frac{5.4}{18} \cdot 500 = 150 \text{ ml}$$

The computation shown above is for illustration purposes only. One skilled in the art will recognize that the correlation of wetted length or area to hydration may depend on the shape of the absorbent article. For example, the absorbent area may be of an elliptical shape or the absorbent area may have varying depth. An appropriate formula for correlating the wetted area to hydration may be developed based on the particular shape, basis weight, and/or capacity profile of the absorbent area.

Alternatively, the altering of the physical or electrical properties may be directly correlated with the amount of hydration in the absorbent article. For example, a change in equivalent resistance may be correlated to the amount of hydration in the absorbent article based on a predetermined relation between the change in resistance and hydration in the absorbent article.

In the following sections, embodiments of hydration device 114 are described in greater detail. However, the specific embodiments of the hydration device 114 described below are not limiting on the invention. Generally, any hydration device having an electrical or physical property capable of being altered by hydration received in the absorbent area, the alteration indicating the amount of hydration, falls within the scope of the invention.

I. Resistor Array Device

In one embodiment of the invention, the resistance of hydration device 114 may be altered by hydration received in absorbent area 112. Hydration device 114 may include an array of resistors. As hydration soaks a length of absorbent area 112 the resistors in the array of resistors may be connected in parallel, thereby reducing an equivalent resistance of hydration device 114. The equivalent resistance of the hydration device may be correlated to, e.g., an amount of hydration or a dimension of the area wetted by the hydration. The amount of hydration may indicate the total loading of the absorbent article. Therefore, equivalent resistance may indicate product loading without requiring a physical inspection of the product.

Figure 2:
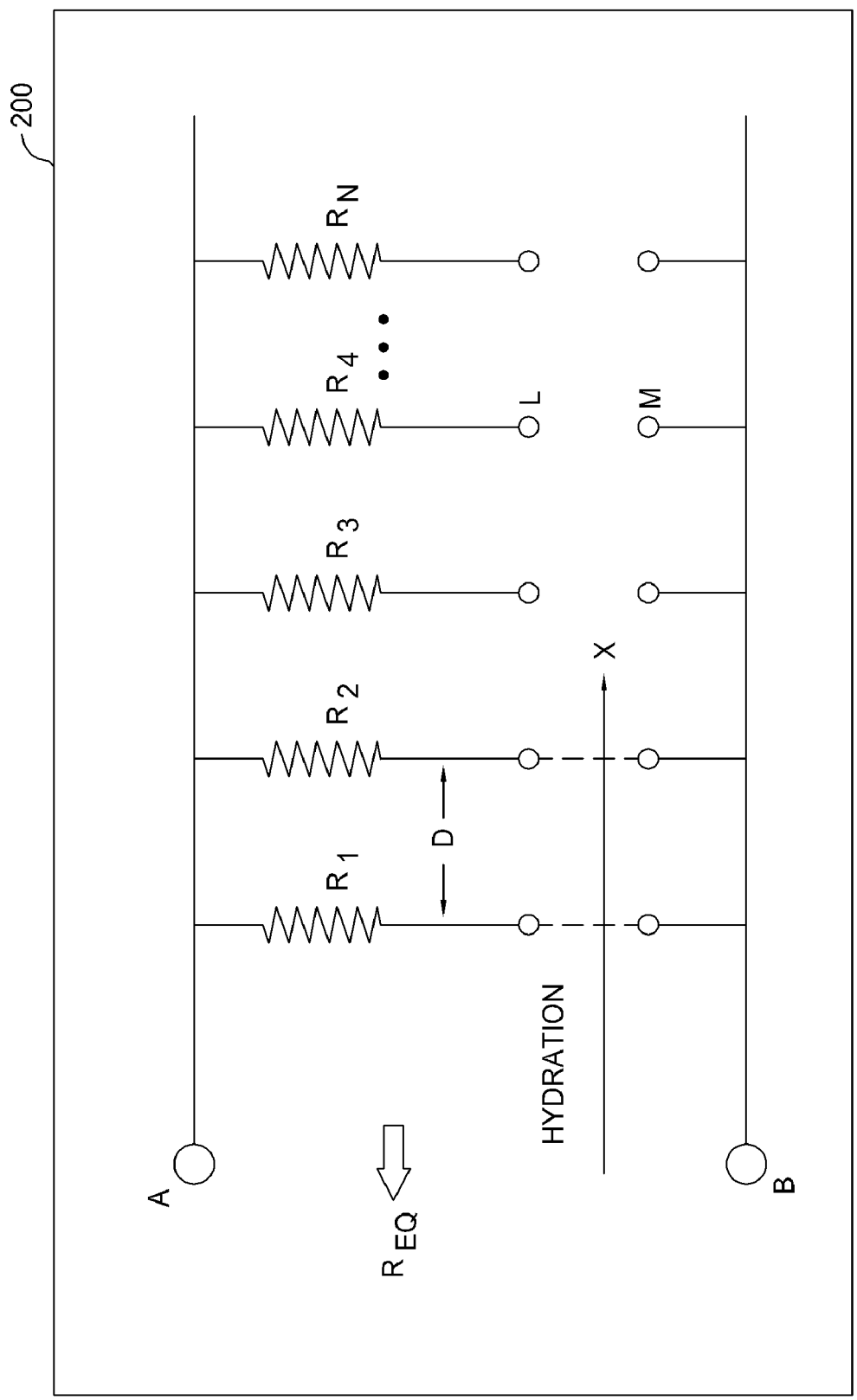
FIG. 2 is an exemplary circuit diagram illustrating an array resistor device according to an embodiment of the invention.

FIG. 2 illustrates an exemplary circuit diagram representing an array resistor device 200, which is one embodiment of hydration device 114 shown in FIG. 1. As illustrated in FIG. 2, array resistor device 200 may include an array of resistors comprising resistors R1, R2, . . . , RN. Resistors R1-RN may be connected to a common node A, as shown in FIG. 2. Furthermore, the resistors R1-RN may be disconnected from a second node B by an open circuit. For example, referring to R4 in FIG. 2, the open circuit between node L and node M disconnects R4 from node B.

When hydration is received in an absorbent article comprising array resistor device 200, the area soaked by the hydration may expand along a length of the absorbent area 112. The hydration, due to its natural conductivity, or through the dissolution of electrolytes disposed on the absorbent article 110, may close one or more open circuits connecting the array resistors from node B. For example, referring back to FIG. 2, hydration is shown expanding in the X direction. As the hydration expands in the X direction, the hydration electrically connects the resistors to node B, thereby connecting the resistors in parallel to one another.

Processing circuit 118 may monitor the equivalent resistance of the array resistor device 200 across nodes A and B. One skilled in the art will recognize that if no hydration is received in the absorbent article, none of the resistors in the resistor array are connected to each other and the equivalent resistance is deemed infinite. However, as the resistors are progressively connected to each other in parallel, the equivalent resistance across nodes A and B begins to drop as each resistor is connected to node B. The equivalent resistance determined by the connected resistors may be computed according to the following equation well known to those skilled in the art:

$$\frac{1}{R_{EQ}} = \frac{1}{R_1} + \frac{1}{R_2} + \ldots + \frac{1}{R_M}$$

wherein REQ is the equivalent resistance measured across nodes A and B and R1-RM are the resistors connected in parallel.

The equivalent resistance may correspond to a wetted length of a hydrated region in the absorbent area 112. For example, the resistors may be strategically placed at a predetermined distance D (shown in FIG. 2) from each other. Accordingly, the connection of one resistor to another may correspond to a length of an area wetted by the hydration, with each additional connection corresponding to an increase in the length of the hydrated area. Therefore, the wetted length may be determined by the number of connected resistors. The number of connected resistors may be ascertained by the equivalent resistance. The number of resistors included in resistor array 200, the distance between the resistors, the location of the resistors, and the like may be selected according to a desired resolution to measure the wetted length.

Figure 3A:
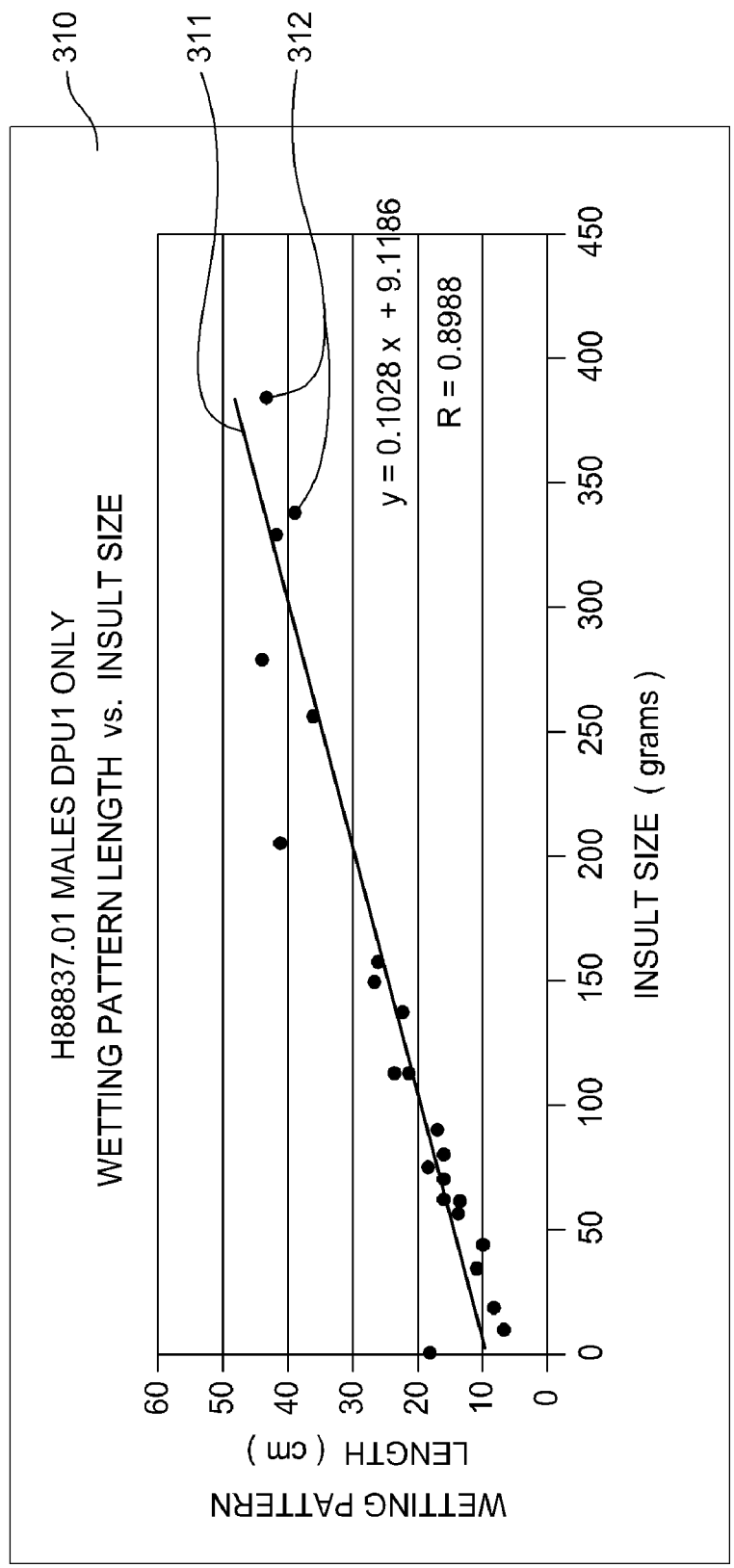
FIGS. 3A and 3B illustrate exemplary charts correlating a dimension of a wetted area to an amount of hydration, according to an embodiment of the invention.
Figure 3B:
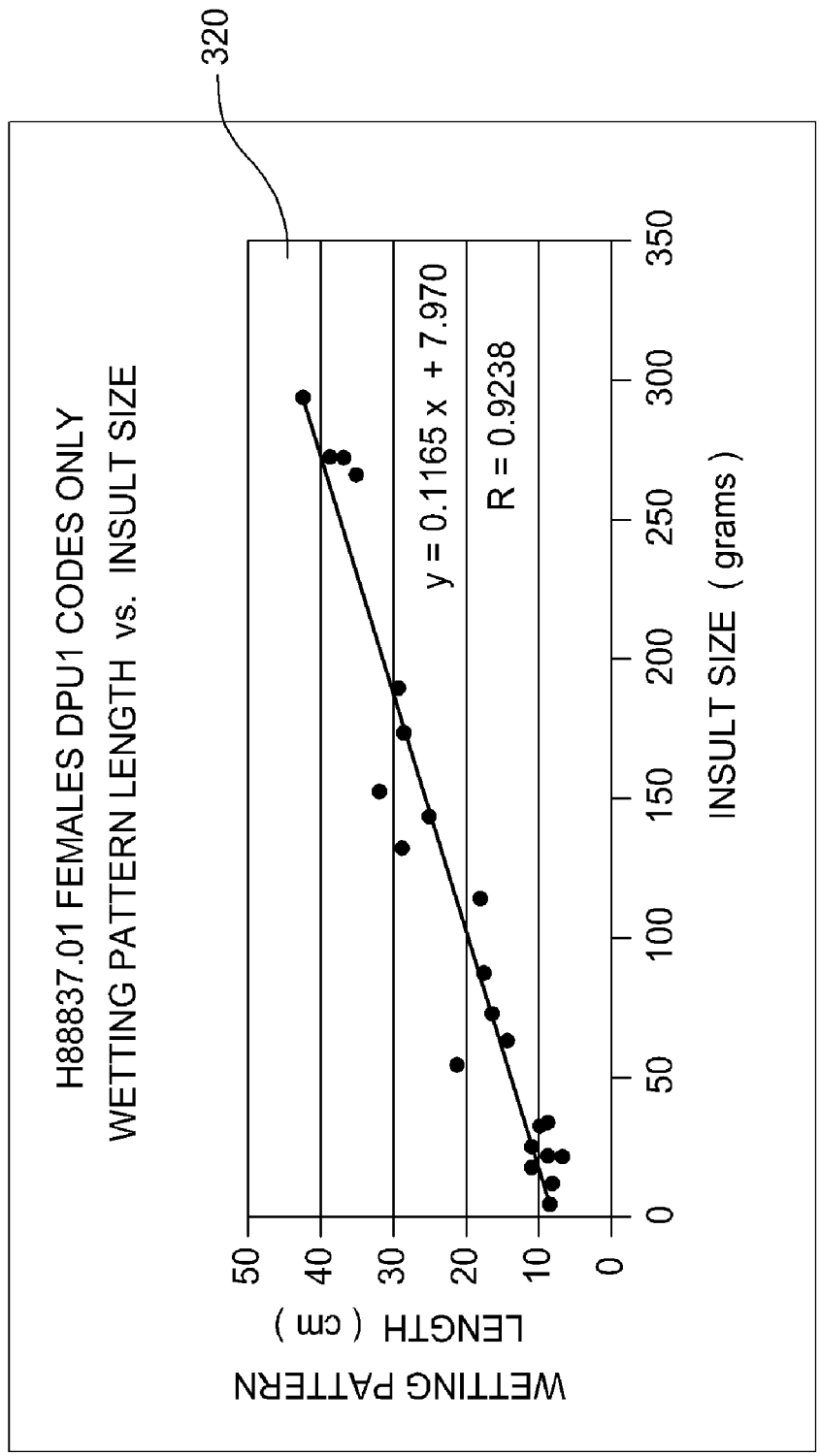

One skilled in the art will recognize that the wetted length of an absorbent area is well correlated to an amount of hydration in the absorbent area. The wetted length—hydration amount correlation may depend on a wide variety of factors including the shape, thickness, uniformity, and the like of the absorbent area. FIGS. 3A and 3B illustrate graphs of exemplary functions that may be used to determine the amount of hydration in the absorbent area based on the computation of a wetted length.

For example, the graph 310 in FIG. 3A illustrates the correlation between wetting pattern length and the insult size for a first product for male subjects. The y axis of graph 310 illustrates the wetting pattern length in increments of 10 centimeters, and the x axis illustrates the insult size in increments of 50 grams. Function 311 may correlate the wetting pattern length to the insult size. Function 311 may be determined, for example, based on test data 312 retrieved during testing of the first product. Graph 320 in FIG. 3B is similar to graph 310 and illustrates a function correlating wetting pattern length to insult size for a second product configured to be worn by female subjects.

While a correlation of equivalent resistance to a wetted dimension, and a correlation of the wetted dimension to an amount of hydration is described herein, one skilled in the art will recognize that the equivalent resistance may be directly correlated to the amount of hydration. For example, the amount of hydration may be determined based on a predefined relation between the equivalent resistance and the amount of hydration.

Figure 4:
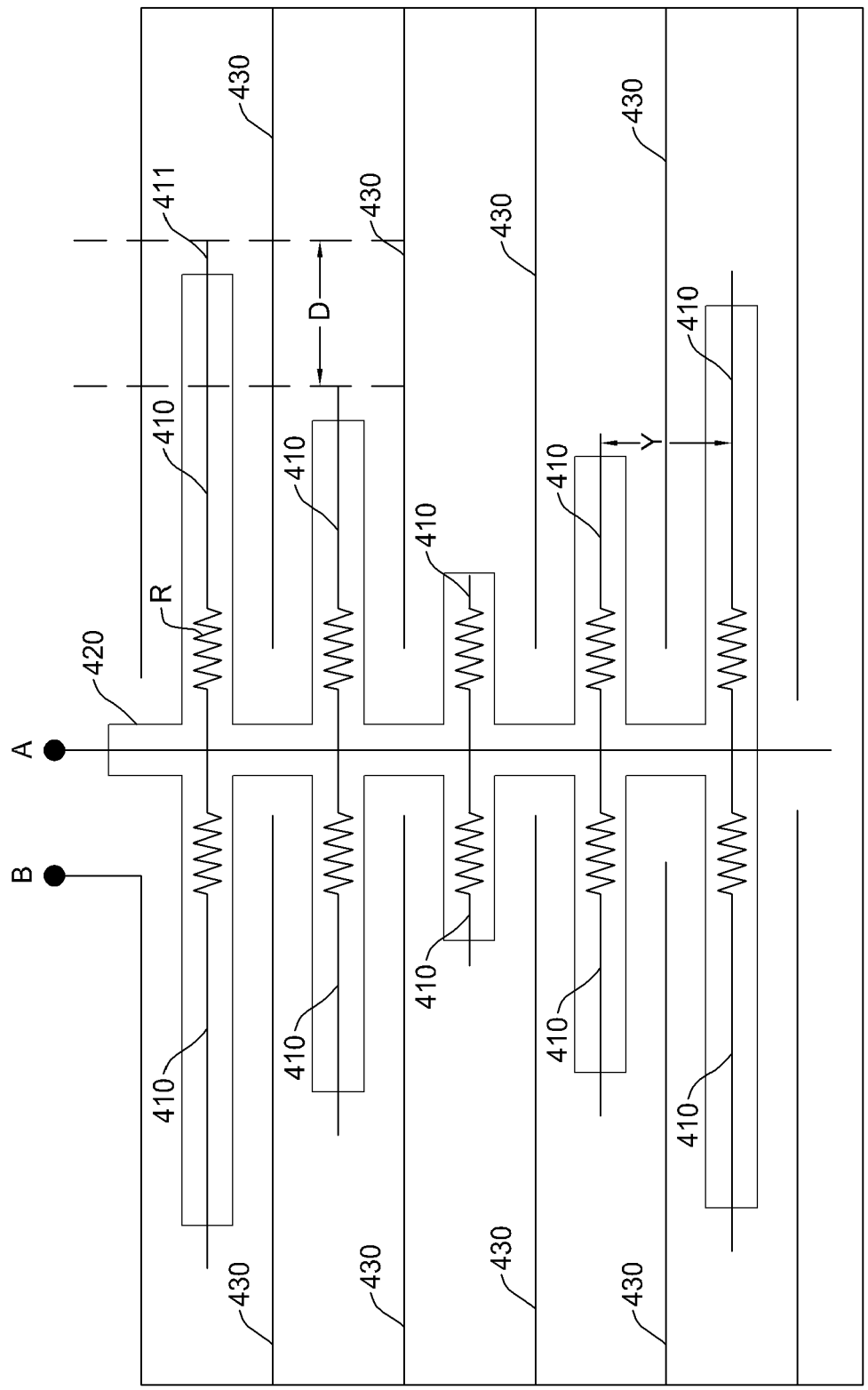
FIG. 4 illustrates an array resistor device according to an embodiment of the invention.

FIG. 4 illustrates an array resistor device 400. Array resistor device 400 is an embodiment of the array resistor device circuit diagram 200 illustrated in FIG. 2. As illustrated in FIG. 4, array resistor device 400 may include a plurality of first conductive lines 410. Each conductive line 410 may be coupled with a resistor R, as illustrated. Furthermore, each of the conductive lines 410 may be associated with a common node A. It should be apparent that node A in FIG. 4 corresponds to node A in the circuit diagram in FIG. 2.

In one embodiment, the conductive lines 410 may be partially covered by an insulative material 420. Insulative material 420 may be configured to prevent contact between hydration received in absorbent area 112 and the conductive lines 410 at locations where the conductive lines are covered by the insulative material. Each conductive line may include a tip 411 that is not covered by the insulative material 420, therefore allowing the tip to be exposed to the hydration.

As illustrated in FIG. 4, the conductive lines 410 may be of variable length, such that the tips 411 of the conductive lines are at predetermined distance from each other. For example, FIG. 4 illustrates a distance D between two tips 411. The predetermined distance between the tips 411 may determine the resolution of the length of the wetted area measured by the array resistor device 400. For example, the smaller the distance D between the tips 411, the greater the precision of measurement of position of the hydration in the absorbent area. Accordingly, in embodiments requiring higher precision a relatively greater number of tips 411 may be placed at relatively smaller distances D from each other.

The array resistor device 400 in FIG. 4 may also include a second set of conductive lines 430. Each conductive line 430 may be associated with a common node B. One skilled in the art will recognize that node B in FIG. 4 corresponds to node B in FIG. 2. Each conductive line 430 may be placed in relative proximity to one or more conductive lines 410. In one embodiment, conductive lines 410 and 430 are affixed to the absorbent article. In another embodiment, conductive lines 410 and 430 are printed on to the absorbent article.

The region between a conductive line 410 and a proximate conductive line 430 forms an open circuit which corresponds to the open circuit between nodes L and M illustrated in FIG. 2. Hydration received at or near a tip 411 may electrically connect a conductive line 410 to a conductive line 430, thereby connecting the resistors R in parallel.

As each conductive line 410 is electrically connected with a conductive line 430, one or more resistors R associated with the conductive lines may be connected in parallel, thereby reducing the equivalent resistance measured between nodes A and B. Furthermore, as described earlier, the equivalent resistance may indicate the number of resistors connected in parallel, and consequently a wetted length of the absorbent area. The wetted length may then be correlated to an amount of hydration in the absorbent area.

Figure 5:
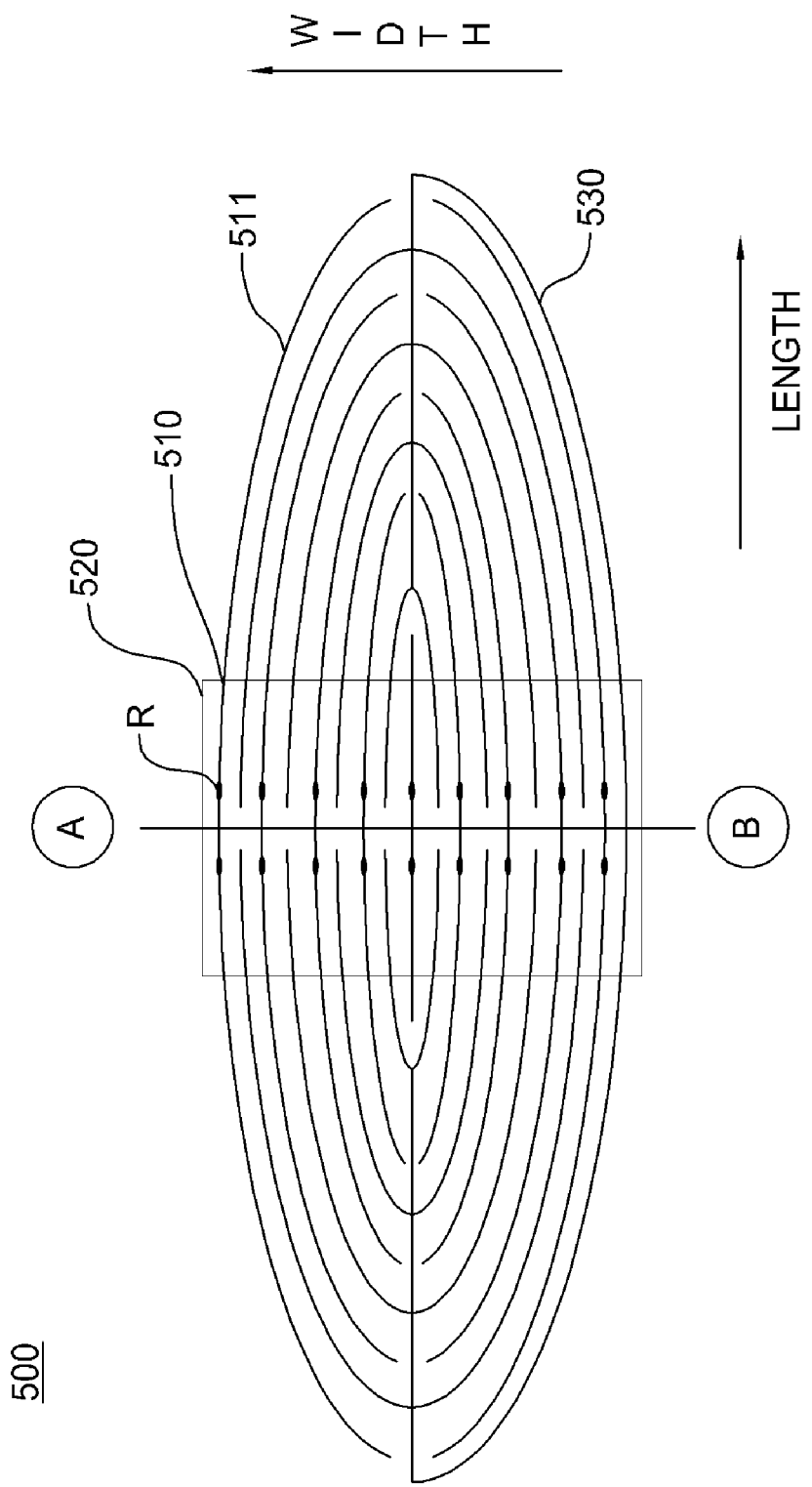
FIG. 5 illustrates another array resistor device according to an embodiment of the invention.

In some embodiments an array resistor device may provide an indication of the expansion of hydration along both the length and/or the width of a wetted region. The length and the width may be used to more accurately determine an estimate of the amount of hydration in the absorbent article. FIG. 5 illustrates an array resistor device 500 that is configured to provide an indication of the expansion of hydration along both the length and the width of a wetted region. Array resistor device 500 is an embodiment of the array resistor device 200 described in FIG. 2.

As illustrated in FIG. 5, array resistor device 500 may include a plurality of conductive lines arranged in an elliptical configuration. As with the embodiment illustrated in FIG. 4, the array resistor device 500 includes a plurality of conductive lines 510. Each conductive line 510 comprises a resistor R and the conductive lines 510 are associated with a node A. The array resistor device 500 also includes a second set of conductive lines associated with a node B. The conductive lines 510 are partially covered by an insulative material 520, as illustrated in FIG. 5.

Due to the shape of the insulative material and the curved (specifically, elliptical) configuration of the conductive lines, conductive lines 510 may be connected to conductive lines 530 regardless of the direction in which the wetted region expands. Therefore, by allowing resistors to be connected in parallel regardless of the direction in which the wetted region expands, a more accurate estimation of the amount of hydration in the absorbent article may be achieved.

Figure 6:
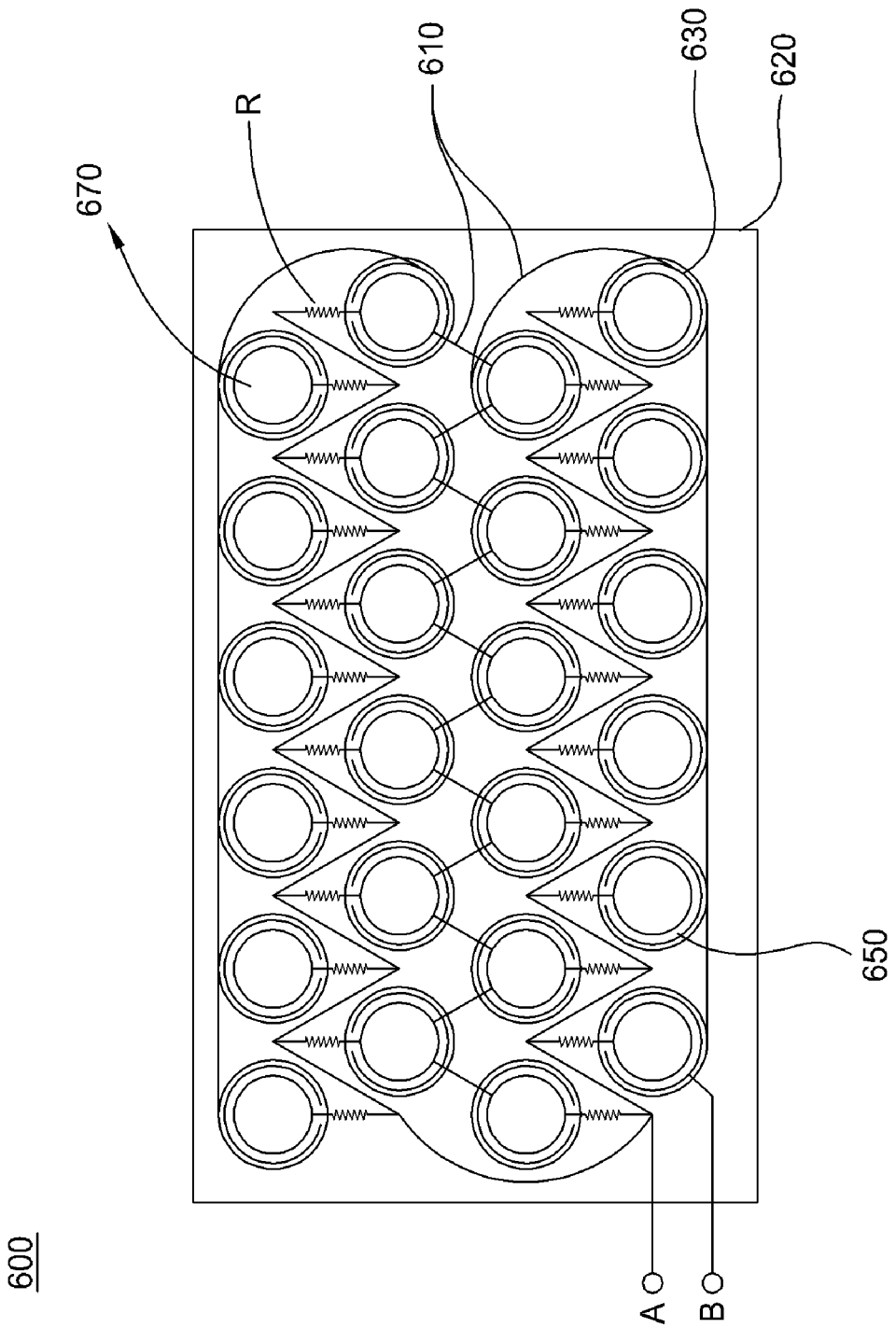
FIG. 6 illustrates yet another array resistor device according to an embodiment of the invention.

In some instances, absorbent area 112 may contain multiple distinct insult points of hydration that are unconnected to each other. An insult point is defined herein as a region in the absorbent area receiving hydration. FIG. 6 illustrates an embodiment of the invention configured to determine the amount of hydration in an absorbent article when multiple insult points are present in the absorbent area.

FIG. 6 illustrates an array resistor device 600 comprising a network of conductive pads 670. Each pad 670 is associated with a resistor R, as shown in FIG. 6. The conductive pads 670 are interconnected by conductive lines 610, as illustrated. A conductive line 630 is disposed in relative proximity to the conductive pads 670 and forming a region 650 between each conductive pad 670 and the conductive line 630. The conductive pads 670 are associated with a common node A, and the conductive line 630 is associated with a node B, as illustrated in FIG. 6. Furthermore, an insulative material 620 may also be provided to isolate the conductive pads 670 from each other.

Region 650 corresponds to the open circuit between nodes L and M illustrated in FIG. 2. Therefore, when hydration is received in region 650, the hydration may electrically connect a conductive pad 670 to the conductive line 630, thereby electrically connecting a resistor R associated with the conductive pad to node B. In the embodiment disclosed in FIG. 6, resistors R may be connected in parallel irrespective of the location in which hydration is received. Therefore, the amount of hydration may be determined even when there are multiple distinct insult points.

Figure 7A:
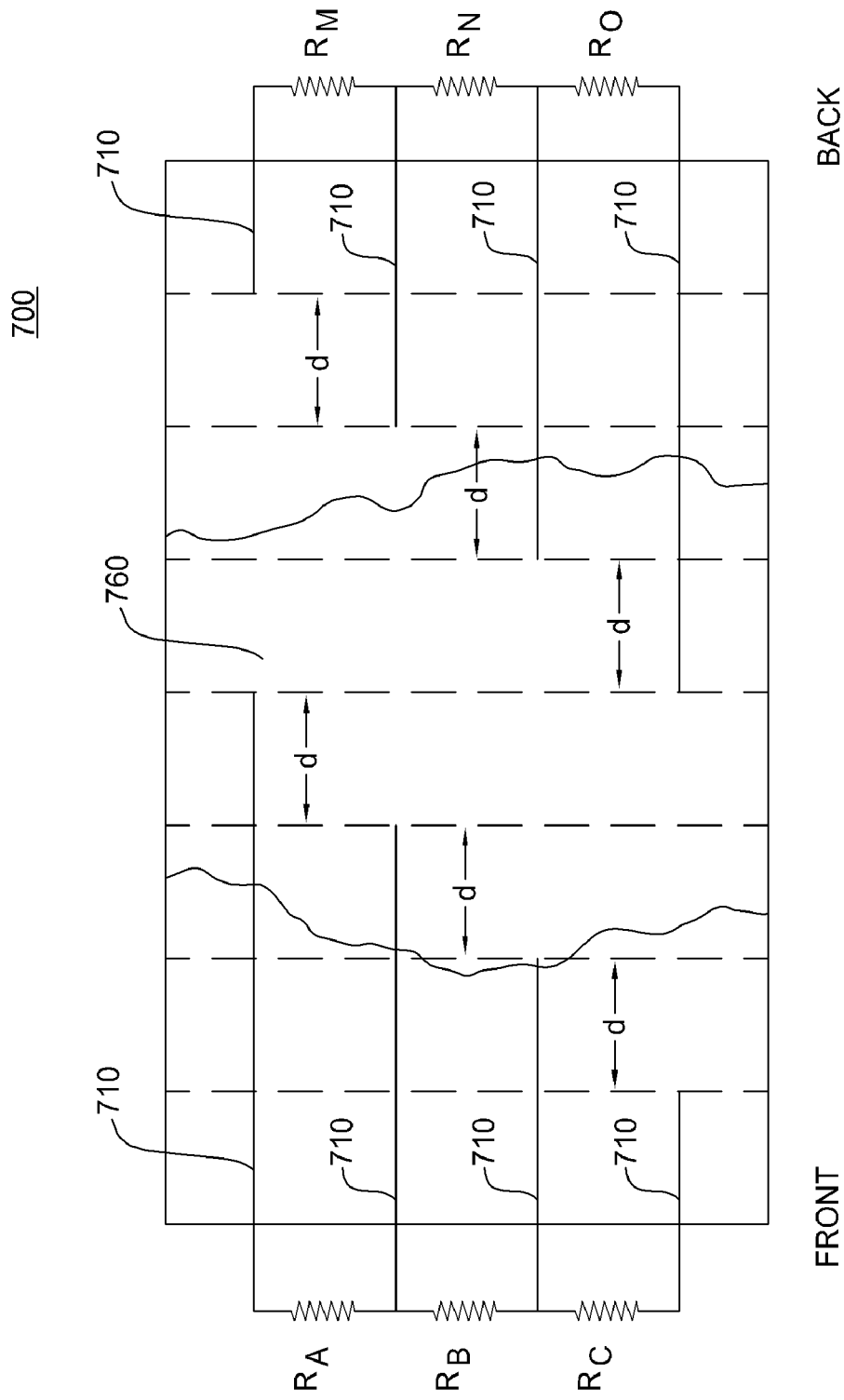
FIG. 7A illustrates a still another array resistor device according to an embodiment of the invention.

FIG. 7A illustrates an alternative embodiment of the array resistor device for measuring a wetted length. As illustrated in FIG. 7, array resistor device 700 may comprise a first set of resistors arranged on a first side of the absorbent area and a second set of resistors arranged on a second side of the absorbent area. For example, in FIG. 7, resistors RA, RB, and RC are shown arranged on the front side of the absorbent area and resistors RM, RN, and RO are arranged along the back side of the absorbent area. Resistors RA, RB, RC, RM, RN, and RO may or may not have the same values.

Variable length conductive lines 710 may extend from the terminals of each resistor into the absorbent area, as illustrated in FIG. 7. The difference between the lengths of the conductive lines (d) may be predetermined and may establish the resolution of the wetted length measured by the array resistor device 700. Therefore, in embodiments requiring high precision measurement, a relatively greater number of conductive lines (and resistors) may be placed at relatively smaller distances d from each other. One skilled in the art will recognize that the lengths d need not be equal to each other.

Processing circuit 118 may monitor the resistance across the terminals of each resistor in the first and second set of resistors. When hydration is received in the absorbent area, the hydration may electrically connect one or more conductive lines, thereby short circuiting a resistor between the connected conductive lines. By determining the resistors that have been short circuited, processing circuit 118 may determine the wetted length. In other words, by determining the specific resistors that have been shorted, processing circuit 118 may determine the length of the wetted region. For example, if resistor RA is shorted, processing circuit 118 may determine that the wetted region extends at least a distance d into the front of the absorbent area.

An exemplary wetted area 760 is illustrated in FIG. 7. As illustrated, the wetted area 760 connects the conductive lines associated with resistors RA, RB, and RO. Therefore, the resistance measured across resistors RA, RB, and RO drops to zero because the resistors are short circuited. Therefore, processing circuit 118 may determine that the hydration has reached the first three conductive strips on the front side and the first two conductive strips on the back side. Based on the number of conductive strips reached by the hydration, processing circuit 118 may determine the wetted length. For example, if the distances d between the conductive strips are equal, processing circuit may determine the wetted length to be 3d for the wetted area 760.

Figure 7B:
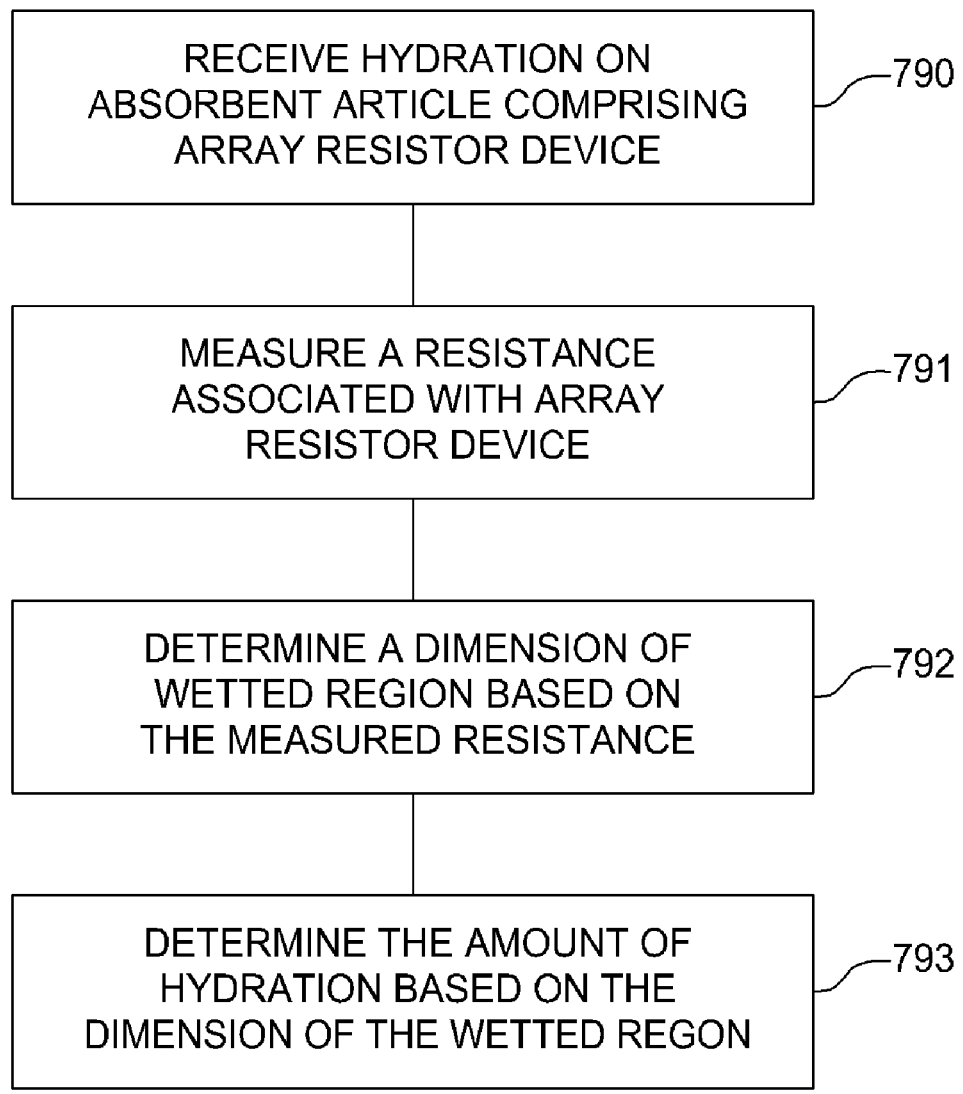
FIG. 7B is a flow diagram of exemplary operations performed to determine an amount of hydration in an absorbent article comprising an array resistor device, according to an embodiment of the invention.

FIG. 7B illustrates exemplary operations performed by processing circuit 118 to determine the amount of hydration in an absorbent article comprising an array resistor device. The operations begin in step 790 by receiving hydration in an absorbent area 112 of an absorbent article 110 containing an array resistor device. The hydration received in the absorbent area may alter a resistance associated with the array resistor device. For example, the hydration may alter an equivalent resistance of the array resistor device or short circuit one or more resistances associated with the array resistor device.

In step 791, processing circuit 118 may measure a resistance associated with the array resistor device. For example, processing circuit 118 may be configured to continuously or periodically measure the resistance of the array resistor device. In step 792, a dimension of the wetted region in the absorbent area may be determined based on the altering of the resistance of the array resistor device. The amount of hydration in the absorbent area may be determined based on the altering of the resistance, in step 793. In some embodiments, the equivalent resistance may be directly correlated to the amount of hydration. For example, the amount of hydration may be determined based on a predetermined relationship between the equivalent resistance and the amount of hydration in the absorbent article.

It is contemplated the number of resistors, the value of the resistors selected and the placement of the resistors in the previously described embodiments is not limiting of the invention. Any number or resistors, resistance values and placement may be used to achieve a desired resolution for measuring a dimension of one or more wetted regions in the absorbent article. For example, in one embodiment, all resistors values may be equal. In other embodiments, the resistor values may be selected to provide a linear drop in resistance as resistors are connected in parallel.

II. Spaced Conductor Device

In one embodiment of the invention, hydration device 114 may include two conductive elements disposed in absorbent area 112 and spaced apart from one another. The conductive elements may not intersect with one another, thereby forming an open circuit between the conductive elements. When hydration is received in the absorbent area, the hydration may electrically connect a portion of the first conductive element to a portion of the second conductive element, thereby altering the resistance between the conductive elements. The altering of the resistance between the conductive elements may provide an indication of a dimension of the area wetted by the hydration, and consequently the amount of hydration.

Figure 8:
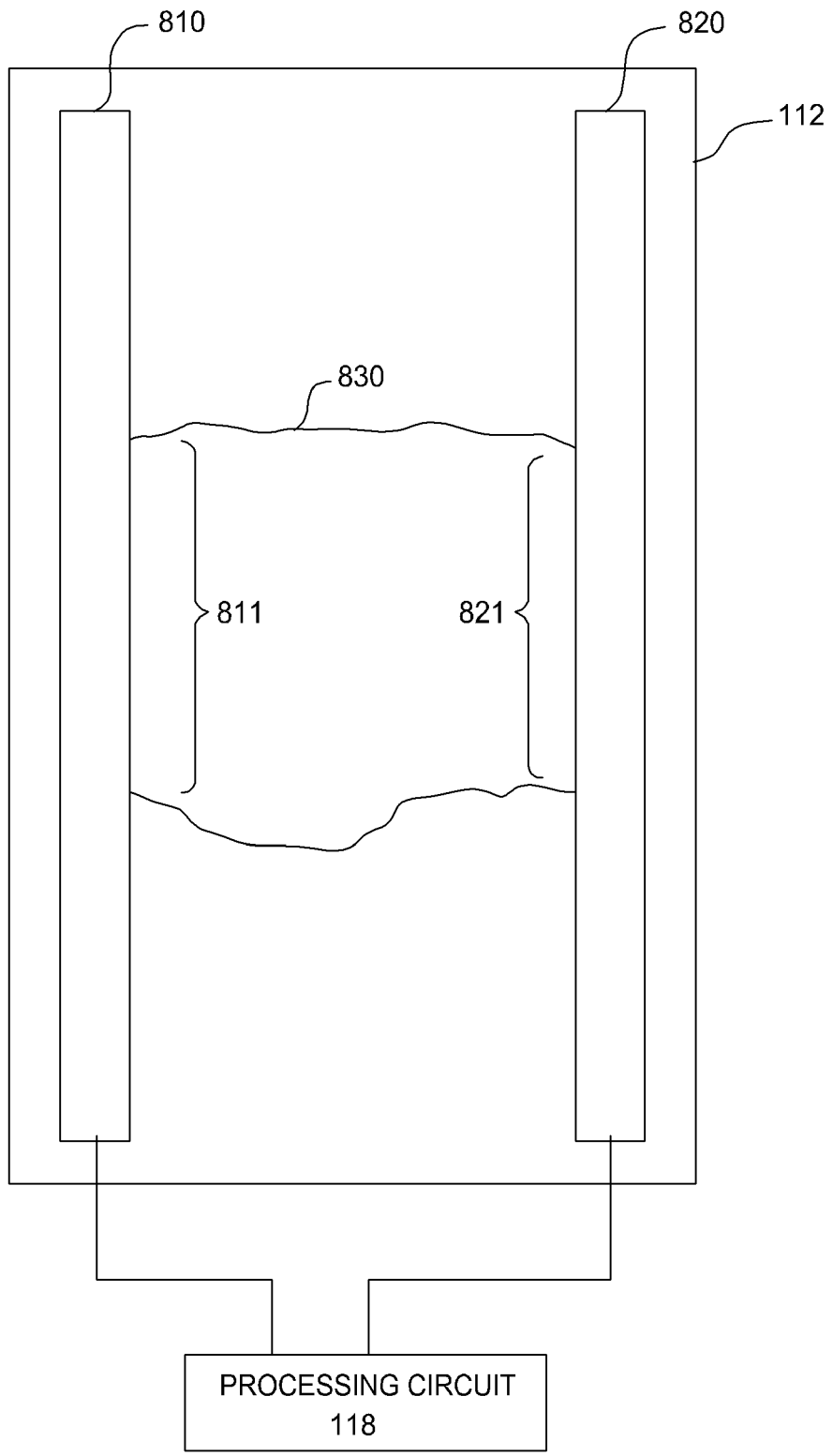
FIG. 8 illustrates a spaced conductor device according to an embodiment of the invention.

FIG. 8 illustrates an exemplary spaced conductor device 800 according to an embodiment of the invention. Spaced conductor device 800 may include a first conductive element 810 and a second conductive element 820 disposed in the absorbent area 112. The conductive elements 810 and 820 may be made from any suitable conductive material such as, for example, conductive thread, conductive foil, conductive ink paste, and the like.

The conductive elements in FIG. 8 are shown extending along the entire length of the absorbent area 112. It is contemplated that any reasonable length and coverage of the absorbent area may be selected to measure hydration in the absorbent article. For example, in a diaper, the conductive elements may extend along a crotch region of the absorbent area where hydration is likely to be received.

The first conductive element 810 and the second conductive element 820 may be spaced apart from one another so that they do not intersect. Therefore, an open circuit may be formed between the first conductive element and the second conductive element when no hydration is present in the absorbent article.

When hydration is received in the absorbent area, the hydration may electrically connect a portion of the first conductive element 810 to a portion of the second conductive element 820, thereby closing the open circuit between the conductive elements. For example, in FIG. 8, wetted region 830 wets a region 811 of the first conductive element 810 and a region 821 of the second conductive element 820 and connects the first and the second conductive element.

As the wetted region expands in the absorbent area 112 the connection between the first conductive element and the second conductive element may alter the resistance between the conductive elements. The resistance may be correlated to a dimension of the wetted region, for example the wetted length or wetted area. The dimension of the wetted region may then be correlated to an amount of hydration in the absorbent article.

Figure 9:
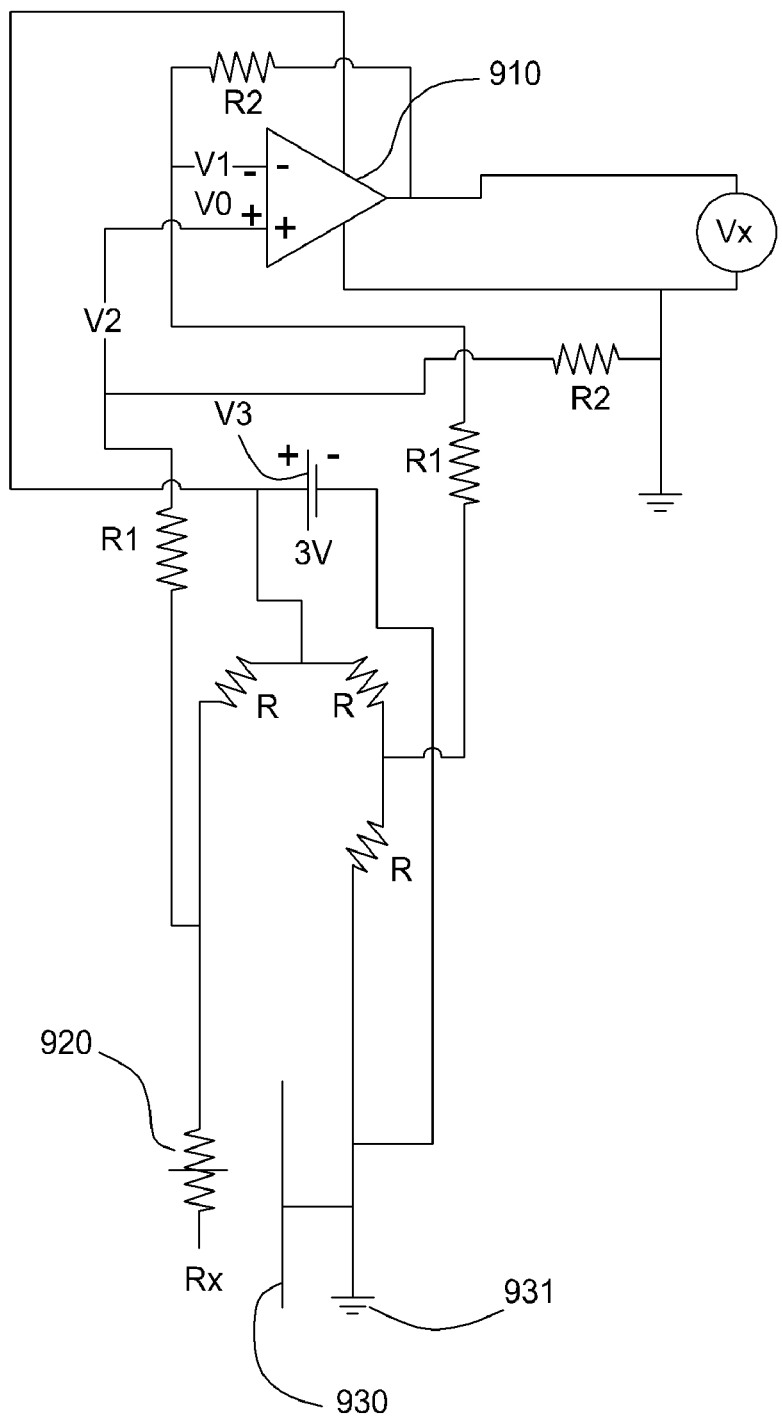
FIG. 9 is a diagram of an exemplary circuit configured to determine resistance changes in a spaced conductor device, according to an embodiment of the invention.

FIG. 9 illustrates an exemplary circuit 900, according to an embodiment of the invention, which determines the resistance between the first conductive element 810 and the second conductive element 820. As illustrated circuit 900 may include a differential operational amplifier 910. A differential amplifier outputs a voltage that is computed by multiplying the difference between the inputs V2 and V1 (also shown as Vo) of the differential amplifier by a constant (gain) factor. For example, in circuit diagram 900, one skilled in the art will recognize that the output voltage Vx of differential amplifier 910 may be determined by equation 1 below:

$$V_x = \frac{R_2}{R_1}(V_2 - V_1), \quad \text{(equation 1)}$$

$$\text{where, } V_0 = V_2 - V_1$$

The value of Vo may be determined by equation 2:

$$V_0 = \frac{1}{2} \cdot V_3 - \left(\frac{R_x}{R_x + R} \cdot V_3\right), \quad \text{(equation 2)}$$

where V3 is the input voltage supplied to the circuit. In one embodiment, as illustrated in FIG. 9, the input voltage V3 may be 3 Volts.

Therefore, combining equations 1 and 2, the output voltage Vx of operational amplifier 910 is determined by equation 3 below:

$$V_x = \frac{R_2}{R_1}\left(\frac{1}{2} \cdot V_3 - \left(\frac{R_x}{R_x + R} \cdot V_3\right)\right) \quad \text{(Equation 3)}$$

As illustrated by equation 3, the output voltage Vx is based on the variable resistance Rx. Variable resistance Rx may be associated with the first conductive element, for example conductive element 810 in FIG. 8. The first conductive element is also referred to hereinafter as the sensing element. Accordingly, the first conductive (sensing) element may carry a fixed potential (voltage) and may determine the value of Rx.

The second conductive element 930 is also shown in FIG. 9 and is also referred to as the grounded element. Accordingly the grounded element 930 is shown connected to ground 931. As the hydration fills the area between sensing element 920 and grounded element 930, the value of resistor Rx may change. As a result of the change in the value of Rx, the value of the differential amplifier output Vx may also change. Therefore, the differential amplifier output may indicate the change in resistance of the spaced conductor device. The change in resistance may then be correlated with a dimension of the wetted area for computation of a volume of the hydration in the absorbent area.

Increasing the resolution of resistance along the length of the sensing element 920 may allow for better differentiation of the position of the hydration in the absorbent area. For example, increasing the ratio of the resistance per unit length of the sensing element 920 to the grounded element 930 may increase the resolution of the dimension of the wetted region.

In one embodiment of the invention the spaced conductor device may include two spaced conductive foils. The first conductive foil may correspond to conductive element 810 and the second conductive foil may correspond to conductive element 820 in FIG. 8, for example. The first conductive foil may be a sensing foil and the second conductive foil may be a grounded foil. The sensing foil may act as a variable resistor, wherein the resistance indicates the wetted length of a region receiving hydration. Therefore, increasing the resolution of the sensing foil with respect to the reference grounded foil may improve the ability to differentiate the position of the hydrated area.

In one embodiment of the invention, to increase the resistance ratio, the composition of the first conductive foil may be selected to be different from the composition of the second conductive foil. For example, the first conductive foil and the second conductive foil may be made from different metals so that the resistance per unit length of the first foil is greater than the resistance per unit length of the second foil.

In one embodiment, the first conductive foil may be doped with a suitable material to increase the resistance per unit length of the first conductive foil in relation to the resistance per unit length of the second conductive foil. For example, the first conductive foil may be doped with carbon to increase the resistance per unit length of the first conductive foil.

In another embodiment, the first conductive foil may be placed under a predetermined amount of tension to stretch the foil. One skilled in the art will recognize that stretching the conductive foil may affect the resistance characteristics of the foil and cause the resistance per unit length to increase.

Figure 10:
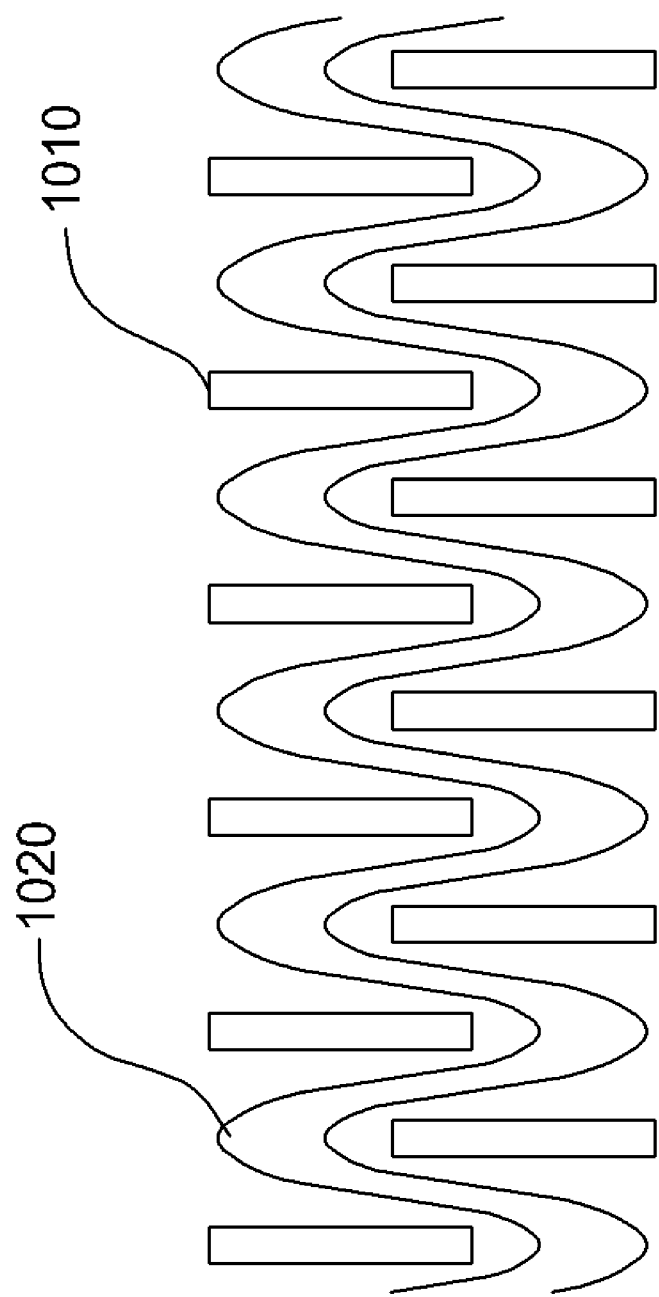
FIG. 10 illustrates a sensing conductor with increased surface area, according to an embodiment of the invention.

In one embodiment of the invention, the surface area of the sensing foil may be increased relative to the surface area of the grounded foil to increase the resistance ratio. FIG. 10 illustrates an exemplary embodiment of a spaced conductor device wherein the surface area of the sensing conductor is increased relative to the surface area of the grounded conductor.

As illustrated in FIG. 10, the surface area of the sensing foil may be increased by winding or folding the sensing foil to expose a greater surface area of the sensing foil to the hydration per unit length. For example, the absorbent area may include a plurality of barriers 1010 interleaved with one another as illustrated in FIG. 10. The sensing foil 1020 may be placed between the barriers 1010 so that the surface area of the sensing foil exposed to the hydration is increased. The barriers 110 may be configured to prevent wound or folded portions of the sensing foil from contacting each other. Barriers 110 may be made from a suitable insulator material, for example, plastic, wood, rubber, glass, nonwovens, thin polymer films, and the like. In one embodiment, barriers 110 may be made from a water permeable material.

Figure 11:
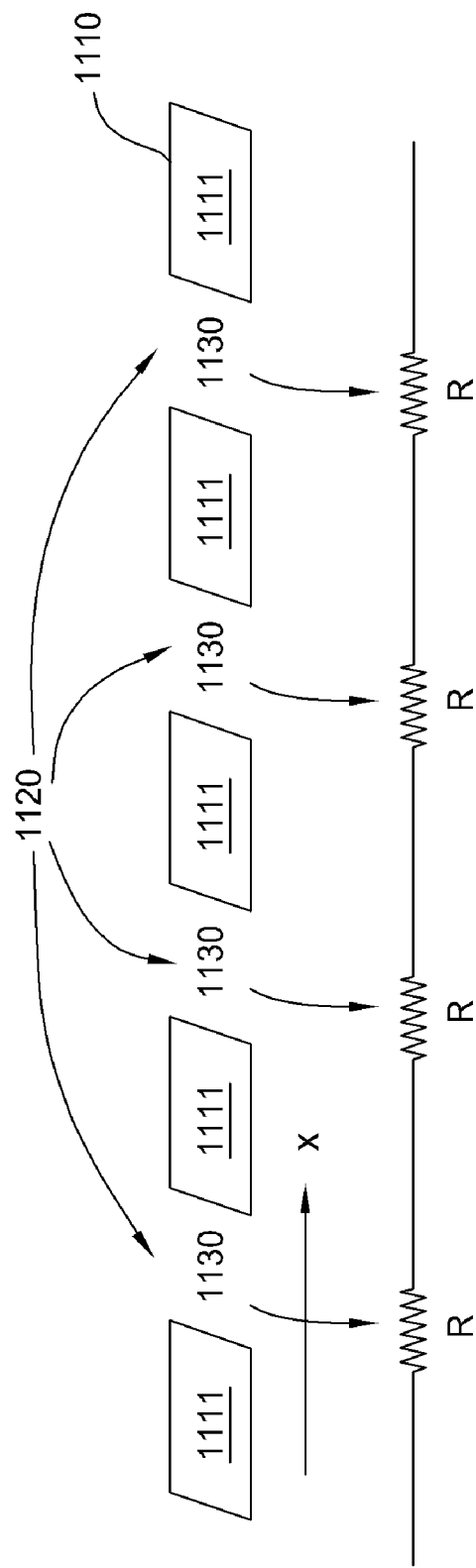
FIG. 11 illustrates a severed sensing conductor according to an embodiment of the invention.

In one embodiment of the invention the sensing foil may be severed at a plurality of locations to create a plurality of discrete regions of higher resistivity (relative to the foil), thereby increasing the resistance per unit length along the length of the severed sensing foil. FIG. 11 illustrates an exemplary severed sensing foil 1110 that is severed at a plurality of locations 1120. Severing sensing foil 1110 may create a plurality of regions 1130 between severed portions 1111 of sensing foil 1110. In some embodiment regions 1130 may be a composed of material that is similar or the same as the material forming absorbent area 112. Therefore, in some embodiments, regions 1130 may be made from non-conductive material. However, it is contemplated that regions 1130 may also be made from conductive materials. For example, regions 1130 may be composed of conductive material of different conductivity than severed portions 1111.

In some embodiments, regions 1130 may be made from material of much higher resistivity in comparison to the sensing foil portions 1111, regions 1130 may act as resistors (R) in series along the length of the sensing foil, as illustrated in FIG. 11, and thereby increasing the resistance per unit length along sensing foil 1110.

As hydration moves along the length of sensing foil 1110, for example in direction x illustrated in FIG. 11, the hydration may soak regions 1130, thereby electrically connecting each severed portion 1111. The resistivity of the soaked regions 1130 may still be much greater than the portions 1111, which are made from a conductive material. Therefore, as the hydration moves in direction x, processing circuit 118 may see a stepped change in resistance as each region 1130 is soaked. The stepped change may allow for better differentiation of the position of the hydrated region in the absorbent area.

In one embodiment of the invention, the conductive elements 810 and 820 may be formed by printing a conductive ink in the absorbent area 112. The conductive ink may include conductive materials and may be formulated for printing on to a substrate, for example, the absorbent area. The conductive ink may include one or more vehicles for the conductive materials, for example, resins and/or solvents. Various other ink additives known in the art, for example, antioxidants, leveling agents, flow agents, drying agents, and the like may also be included in the conductive ink. The composition of the conductive ink may be adjusted by a skilled practitioner for a desired rheology.

The conductive materials in the conductive ink may include any combination of silver, copper, gold, palladium, platinum, and like conductors. The conductive material may be flakes and/or powders. The amount of conductive material in the ink may be selected to achieve a desired resistance per unit length for each conductive element. The resin in the conductive ink may include polymers, polymer blends, fatty acids, and the like. Alkyd resins, refined linseed oil based resins, soy resins may also be used.

Solvents in the conductive ink may include any combination of hydrocarbon solvents, water, alcohols, for example, isopropyl alcohol, and the like. In one embodiment, an aliphatic hydrocarbon solvent is employed. Any reasonable amount of solvent may be mixed into the conductive ink. Factors affecting the amount of solvent mixed include viscosity of the resin, solvation characteristics of the solvent, conductive particle size, distribution and surface morphology of the printing method employed and the like. More generally, solvent may be added to an ink mixture until a desired rheology is achieved. The desired rheology, for example, may depend on the type of printing process used.

The conductive ink may be printed on to the absorbent area using printing techniques known in the art of printing inks on paper and other substrates. Exemplary printing techniques include offset lithographic (wet, waterless, and dry) printing, flexographic printing, rotogravure (direct or offset) printing, intaglio printing, ink jet printing, electrophotographic (laser jet and photocopy) printing, letter press printing, and the like.

In some embodiments, the conductive ink may be printed to form distinct portions of a sensing foil similar to, for example, the severed portions 1111 illustrated in FIG. 11. Therefore, the sensing element may sense a stepped change in resistance as the hydration moves along the length of the printed sensing element.

Figure 12:
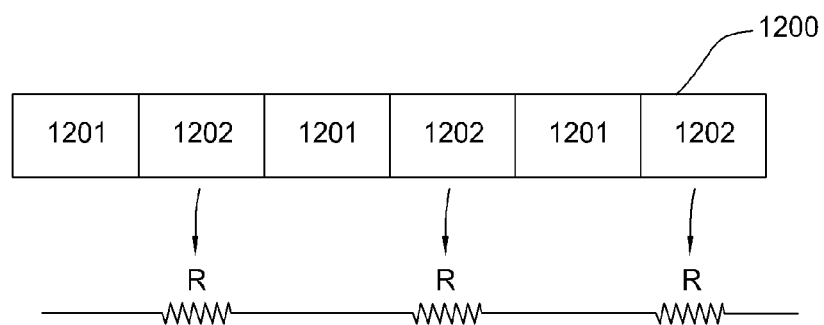
FIG. 12 illustrates a sensing conductor made from printed ink according to an embodiment of the invention.

In one embodiment, different inks may be used to create a stepped change in resistance. FIG. 12 illustrates a printed sensing element 1200 made from different inks. As illustrated sensing element 1200 may be made of a plurality of sections made from a first type of ink 1201, and a plurality of sections of a second type of ink 1202. The second type of ink 1202 may have a higher resistivity in comparison to the first type of ink. Therefore, the second type of ink may act as resistors in series along the length of sensing element 1200, thereby providing a stepped change in resistance and increasing resolution.

In one embodiment of the invention, the sensing element may be made from a conductive thread. The conductive thread may be made from a fiber based material for example cotton or a suitable polymer based material. The conductive thread may include conductive material disposed in the thread. As the hydration received in the absorbent area soaks the thread, the cellulosic fibers of the thread may expand, thereby increasing the distance between the conductive materials disposed in the thread. As a result of the increase in the distance between the conductive materials, the resistance along the soaked length of the thread may increase. The increase in the resistance of the thread may provide an increased resolution of resistance. The resolution of the resistance may depend, for example, on the type and amount of conductive material disposed in the thread.

Figure 13:
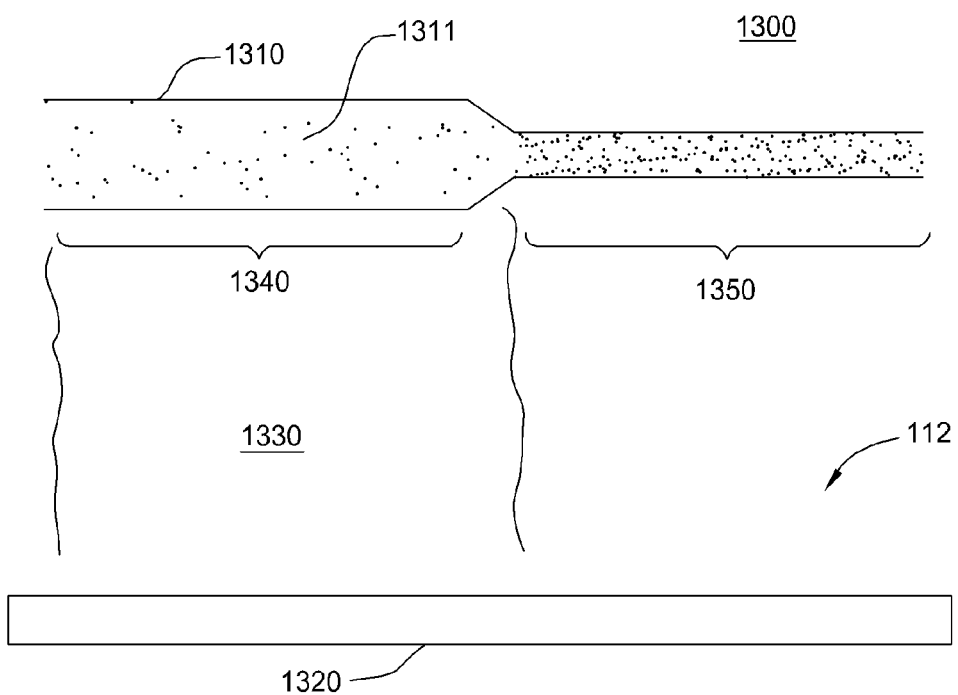
FIG. 13 illustrates a sensing conductor made from a conductive thread, according to an embodiment of the invention.

FIG. 13 illustrates a spaced conductor device 1300 comprising a conductive thread. As illustrated, spaced conductor device 1300 includes a conductive thread 1310 which acts as the sensing element, and a grounded foil 1320 disposed in an absorbent area 112. Conductive thread 1310 may include conductive material 1311 disposed in the thread, as illustrated.

When hydration is received in the absorbent area 112, the hydration may cause the fibers of the thread to expand. For example, wetted region 1330 causes the thread to expand along a soaked length of the thread 1340. Accordingly, the soaked length of the thread 1340 is shown as being larger in size than the length 1350 of the conductive thread that has not been soaked.

The expansion of fibers along the soaked length 1340 may increase the distance between the conductive materials 1311 in the soaked length of the thread. For example, in FIG. 13 illustrates an increased distance between conductive materials 1311 along the soaked length 1311 in comparison to the non-soaked length 1350. The increased distance between the conductive materials 1311 may increase the resistance along the soaked length thereby increasing the resolution of resistance along the sensing thread element 1310.

Figure 14:
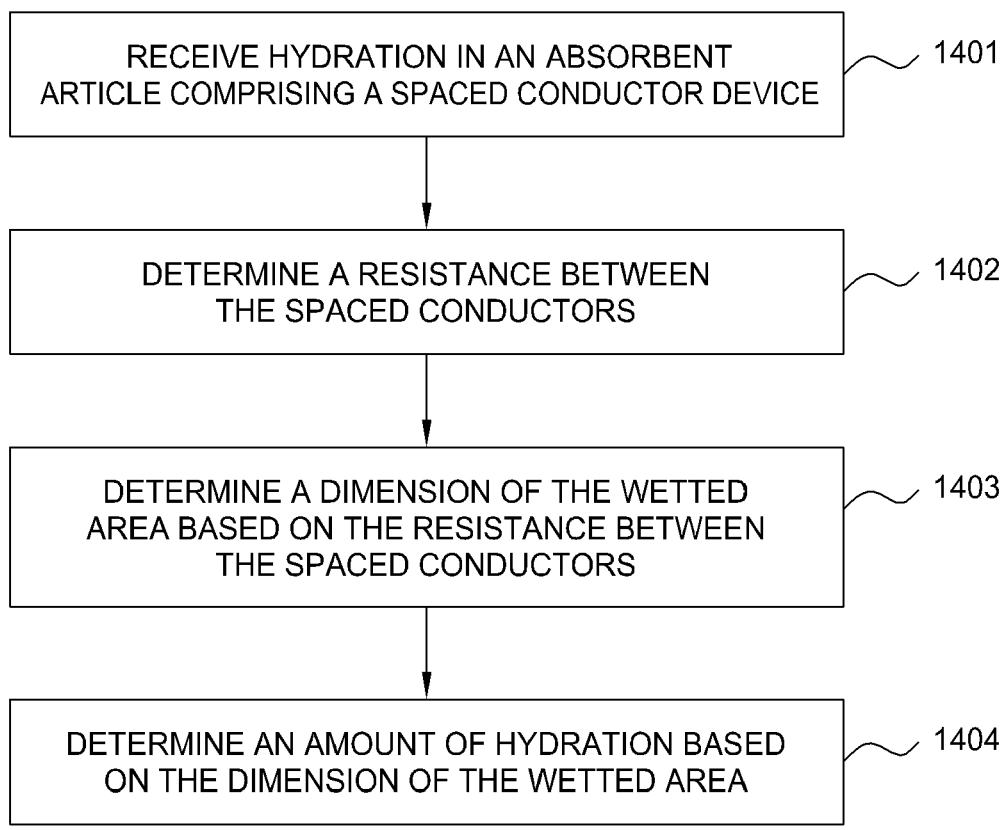
FIG. 14 is a flow diagram of exemplary operations performed to determine an amount of hydration in an absorbent article comprising a spaced conductor device, according to an embodiment of the invention.

FIG. 14 is a flow diagram illustrating exemplary operations performed by processing circuit 118 to determine the amount of hydration in an absorbent article comprising a spaced conductor device. The operations begin in step 1401 by receiving hydration in an absorbent area 112 of an absorbent article 110 containing an array resistor device. The hydration received in the absorbent area may alter a resistance between two spaced conductive elements of the spaced conductor device, as previously described. The conductive elements may be made from a conductive foil, conductive ink, or a conductive thread, previously described. The hydration may alter a resistance between the spaced conductive elements.

In step 1402, processing circuit 118 may measure the resistance between the spaced conductive elements. For example, processing circuit 118 may be configured to continuously or periodically measure the resistance between the spaced conductive elements. In step 1403, a dimension of the wetted region in the absorbent area may be determined based on resistance between the conductive elements. The amount of hydration in the absorbent area may be determined based on the measured resistance, in step 1404.

III. Wick Based Device

The shape of an absorbent core 112 may change during the use of absorbent article 110. For example, in one embodiment, absorbent article 110 may be a diaper. The absorbent core in a diaper may be subject to wide variations in shape during use of the diaper. For example, the shape of the absorbent core when a person wearing the diaper while standing may be different from the shape of the absorbent core when the person is sitting.

The variation in shape of the absorbent area may affect the dimensions of a wetted region, thereby affecting the accuracy of the amount of hydration measured by processing circuit 118 using hydration device 114. The accuracy of the measurement may also be affected by local variations in the fluff and the amount of super absorbent material (SAM) in the absorbent area which may cause variations in the amount of hydration absorbed in such areas.

Furthermore, the shape and size of absorbent core 112, the material from which the absorbent core is made, and the like may differ based on the nature of the absorbent article in which the absorbent core is integrated, and the nature of use of the absorbent article. For example, the size, shape, material, etc. of an absorbent area incorporated in a diaper may be different from the size shape, material etc. of an absorbent area incorporated into a bandage. Therefore, the correlation between the alteration of an electrical or physical property and a dimension of a wetted area, and the correlation between the dimension of the wetted area and the amount of hydration may have to be separately computed for each absorbent article.

Figure 15:
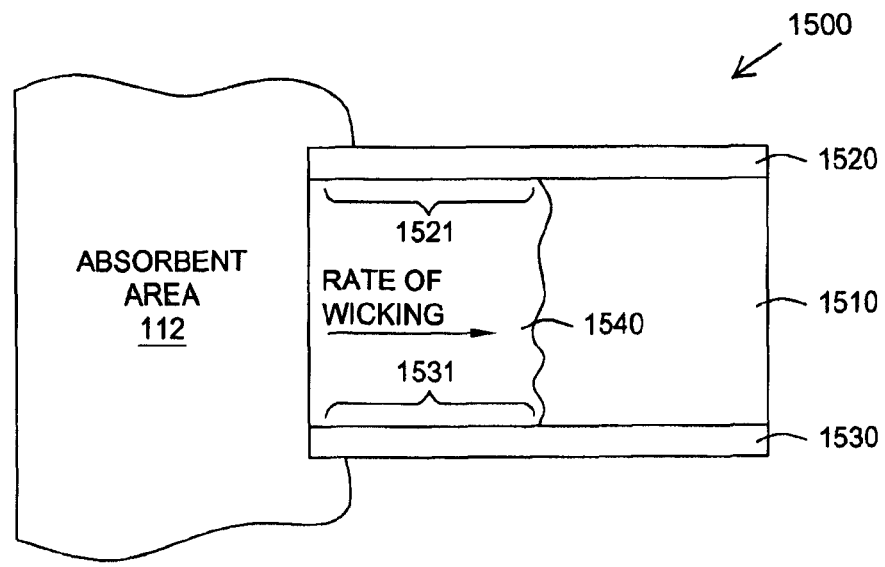
FIG. 15 illustrates a wick based device according to an embodiment of the invention.

In one embodiment of the invention, hydration device 114 may include a wick based device for measuring an amount of fluid in the absorbent area. The wicking device may provide an indication of the amount of hydration in the absorbent article irrespective of the physical shape, size, material, etc. of the absorbent area. FIG. 15 illustrates a wicking device 1500. As illustrated in FIG. 15, wicking device may comprise a wick 1510, and two conductive elements 1520 and 1530 on either side of the wick.

Wick 1510 may be made of any suitable material configured to soak up hydration from the absorbent area. Accordingly, a portion of the wicking device may be coupled with the absorbent area. In one embodiment, wick 1510 may be made from chromatography paper, filter paper, and the like. When hydration is received in the absorbent area, some of the hydration may be absorbed by wick 1510 along a length of the wick.

The length of the wick soaked by the hydration may depend on the amount of hydration received in the absorbent area. For example, for greater amounts of hydration in the absorbent core, the greater amount of hydration is soaked up by the wick. The greater the amount of hydration soaked up by the wick the greater may be the length of the wick soaked by the hydration in the absorbent core. Therefore, the length of the wick soaked may indicate the amount of hydration in the absorbent core.

The rate at which the hydration is soaked up by the wick may vary over time. For example, at the time the wick is first exposed to the hydration, the wick may soak up the hydration relatively quickly. The rate of wicking, however, may decrease over time. The rate of wicking may also depend on the amount of hydration present in the absorbent article. For example, if a large amount of hydration is introduced in the absorbent area, the initial wicking rate may be significantly higher than the initial wicking rate if only a small amount of hydration is introduced.

If multiple hydration events (insults) occur, the wicking rate may increase at the time of each hydration event. For example, a first hydration event may occur in the absorbent area. The wick may soak up some of the hydration at a high wicking rate initially. The wicking rate may gradually slow down and finally stop when the wick is soaked to a length indicating the amount of hydration in absorbent area. If a second hydration event occurs, the wick may soak up more hydration, initially at a high wicking rate and gradually slow down again.

Therefore, the changes in the rate of wicking and the length of the wick soaked by the hydration may indicate the amount of hydration in the absorbent area and the hydration of the person. In other words, the length of the wick soaked may indicate the amount of hydration in the absorbent article. The changes in the rate of wicking may be correlated with distinct hydration events. Determining the time at which the hydration events occur may contribute to the analysis of the hydration of a person wearing the absorbent article. For example, the time period between the hydration events may indicate the hydration of the person.

Conductive elements 1520 and 1530 may be made from a material similar to materials described in the spaced conductor embodiment in the previous section. For example, conductive elements 1520 and 1530 may be made from any combination of a conductive foil, conductive ink, conductive thread, and the like.

Processing circuit 118 may monitor the resistance between conductive elements 1520 and 1530. As hydration is soaked up by wick 1510, the hydration soaked by the wick may electrically connect a portion of conductive element 1520 to a portion of conductive element 1530, thereby changing the resistance between the two conductive elements. For example, in FIG. 15, hydration 1540 soaks a length of wick 1510 connecting a portion 1521 of conductive element 1520 to a portion 1531 of conductive element 1530.

Processing circuit 118 may also monitor the rate of wicking along wick 1510. For example, processing circuit may monitor the rate of change of resistance between the first conductive element 1520 and the second conductive element 1530. The rate of change of resistance may indicate the rate at which hydration is moving along the length of wick 1510, and therefore indicating the wicking rate. Processing circuit 118 may use the resistance between the conductive elements and the rate of wicking to determine the amount of hydration in the absorbent area.

Because wick 1510 is not subject to variations in shape and size, wick 1510 may provide a more constant resistance and a resistance change along the length of the conductive elements in comparison to the absorbent area. Therefore, a more accurate estimation of the amount of hydration in the absorbent area may be achieved.

In one embodiment, the wick may be altered to soak in one direction. Therefore, when the absorbent area is wetted, the wick in contact with the absorbent pad may soak in a direction perpendicular to the electrodes and connecting the electrodes, thereby changing resistance between electrodes in the region directly in contact with the wetted region, and providing an accurate length of the wetted region.

Figure 16:
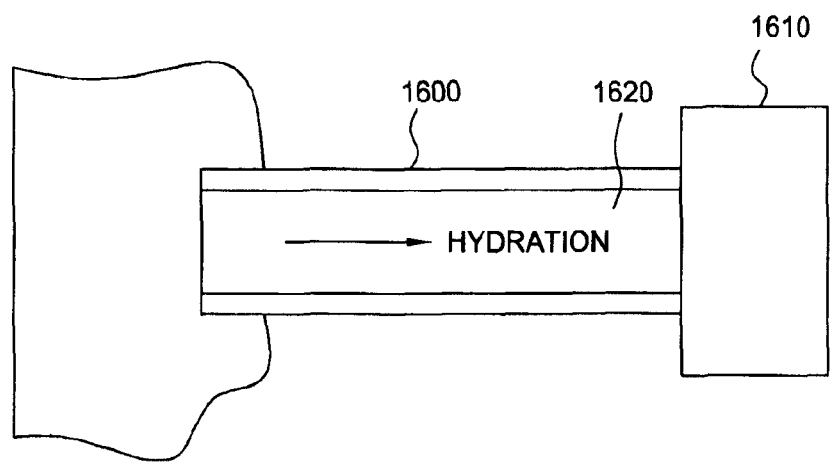
FIG. 16 illustrates a wick based device comprising a hydration alarm, according to an embodiment of the invention.

In one embodiment of the invention a hydration alarm may be installed at the end of a wicking device. FIG. 16 illustrates a wicking device 1600 having a hydration alarm 1610 coupled with a wick 1620. If the hydration soaking the wick 1620 reaches the hydration alarm 1610, or a predetermined resistance value, hydration alarm may be configured to indicate that the absorbent article is full and must be changed. For example, hydration may soak the entire length of the wick and reach hydration alarm 1610. The hydration alarm 1610 may include a temperature sensor to detect the hydration. Alternatively, hydration alarm may include an open circuit which may be closed by the hydration reaching the hydration alarm, thereby indicating presence of hydration at the hydration alarm. Upon detecting the hydration, hydration alarm 1610 may provide an indication that the absorbent article is full.

The indications provided by hydration alarm 1610 may include visual indications, for example, a change in color or visibility of a printed area of the absorbent article. In one embodiment, hydration alarm 1610 may be configured to send a wireless signal to set off an audible alarm to notify a caregiver regarding the status of the absorbent article.

Figure 17:
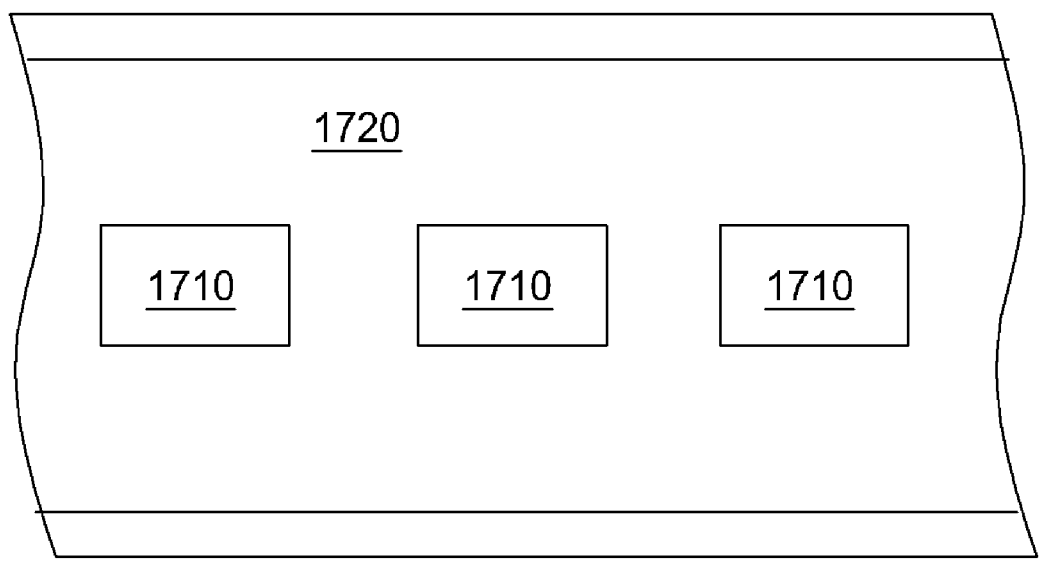
FIG. 17 illustrates a wick based device configured to provide a stepped resistance change according to an embodiment of the invention.

In one embodiment of the invention, the resolution of the resistance measured by the wicking device may be improved by introducing a plurality of areas of different conductivity in the wick. FIG. 17 illustrates an exemplary wicking device 1700 with increased resistance resolution. As illustrated in FIG. 17, the wick of wicking device 1700 includes a plurality of zones 1710. Zones 1710 may have a different conductivity than the area 1720 of the wick. Therefore, as the hydration moves along the length of the wick, processing circuit 118 may see a stepped change in resistance between the conductive elements coupled with the wick, thereby increasing the resolution of resistance.

Figure 18:
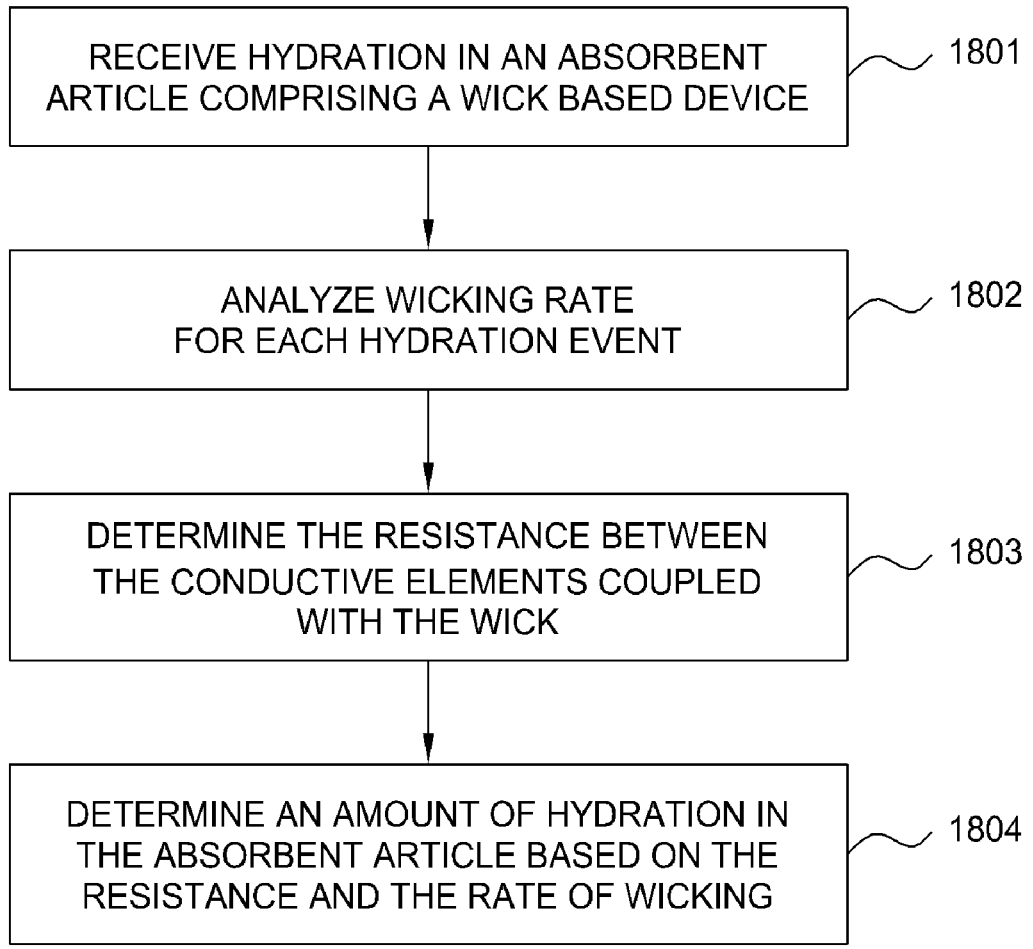
FIG. 18 is a flow diagram of exemplary operations performed to determine an amount of hydration in an absorbent article comprising a wick based device, according to an embodiment of the invention.

FIG. 18 is a flow diagram illustrating exemplary operations performed by processing circuit 118 to determine the amount of hydration in an absorbent article comprising a wick based device. The operations begin in step 1801 by receiving hydration in an absorbent area 112 of an absorbent article 110 containing a wick based device. The hydration received in the absorbent area may soak a wick associated with the wicking device. The wick may connect a portion of a first conductive element to a portion of a second conductive element, thereby altering a resistance between the conductive elements. The conductive elements may be made from a conductive foil, conductive ink, or a conductive thread, previously described.

In step 1802, processing circuit 118 may analyze the wicking rate for each hydration event. For example, processing circuit 118 may analyze the rate of change of resistance across the conductive elements and the resistance between the spaced conductive elements. For example, processing circuit 118 may be configured to continuously or periodically measure the resistance between the spaced conductive elements. The rate of change of resistance may indicate the number of hydration events in the absorbent article, and the time period between the hydration events. Therefore, by correlating the amount of hydration, time period between hydration events, and the like, the hydration of the person may be determined.

In step 1803, processing circuit 118 may determine a resistance between conductive elements coupled with the wick. The length of the wick soaked by the hydration may be determined based on the change in resistance. In step 1804, the amount of hydration in the absorbent article may be determined based on the length of the wick soaked by the hydration and the rate of wicking.

IV. Printed Ruler

In some embodiments of the invention, hydration received in the absorbent area may alter a physical property of hydration device 114. The physical alteration may indicate the amount of hydration in the absorbent area. For example, the physical alteration may be correlated to a dimension of a wetted region in the absorbent area, and the dimension of the wetted area may itself be correlated to the amount of hydration in the absorbent area.

In one embodiment of the invention, hydration device 114 may include a ruler printed on a surface of absorbent article 110. Hydration received in the absorbent area may alter a visual property of the printed ruler. For example, in one embodiment, a portion of the printed ruler may disappear in response to receiving hydration in the absorbent article. The portion of the printed ruler that disappears may be correlated to a dimension of a wetted region in the absorbent area.

One skilled in the art will recognize that the invention is not limited to disappearing rulers. In alternative embodiments, a portion of an invisible ruler may be made to appear, or alternatively, the color of a portion of a printed ruler may be changed to indicate the dimension of the wetted region, and therefore the amount of hydration in the absorbent article.

Any type of ink known in the art for appearing, disappearing, or changing color, triggered by moisture, may be used to make the printed ruler.

Figure 19:
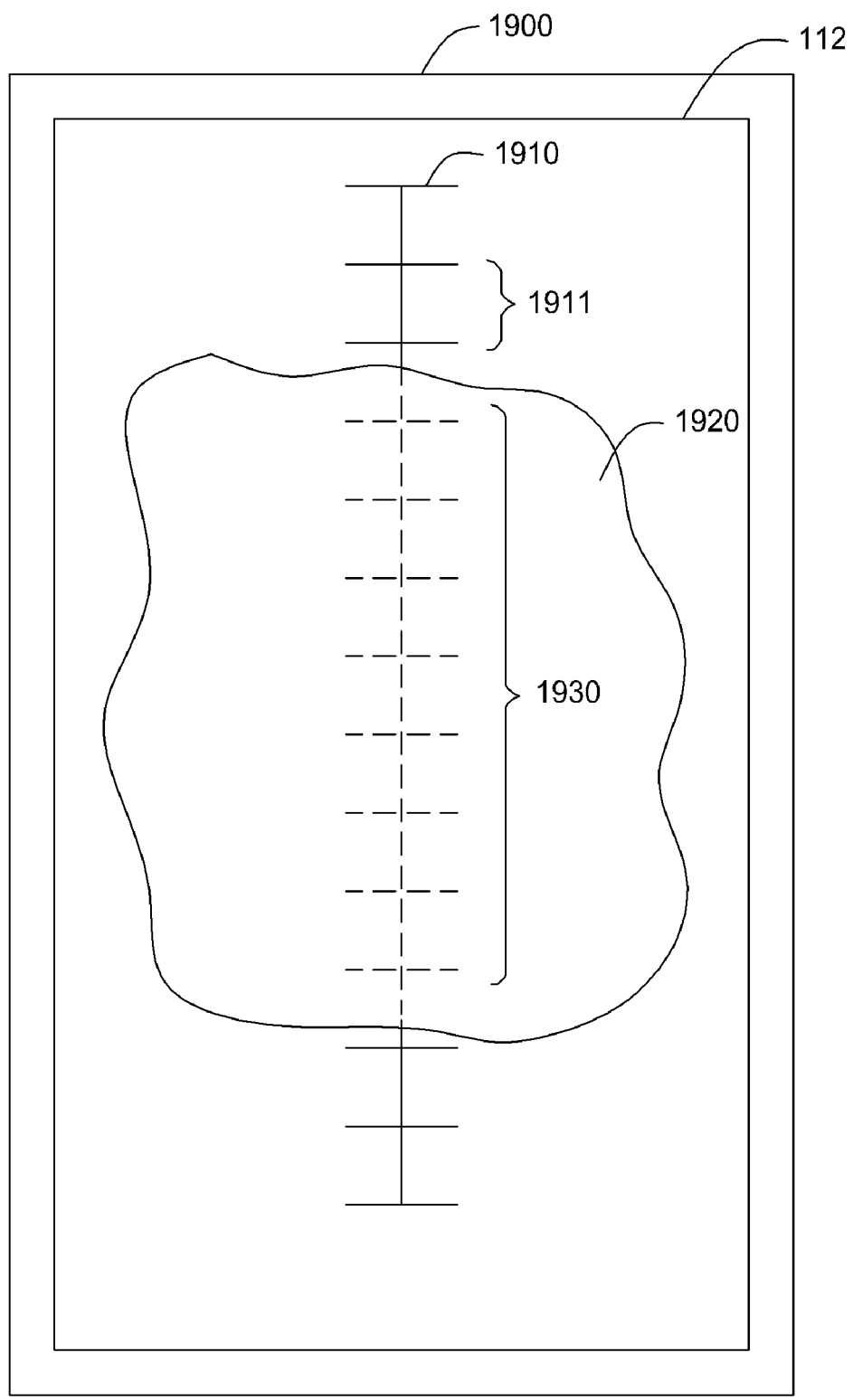
FIG. 19 illustrates a printed ruler according to an embodiment of the invention.

FIG. 19 illustrates an absorbent article 1900 including a printed ruler 1910. Printed ruler 1910 may be disposed along a length of an absorbent area 112 wherein hydration is likely to be received. Hydration received in the absorbent area 112 may alter the visual characteristics of a portion of ruler 1910. For example, hydrated area 1920 may cause the visual characteristics of a portion 1930 of printed ruler 1920. The portion 1930 may disappear, appear, or change in color in response to receiving the hydration.

In one embodiment of the invention the spacing 1911 of printed ruler 1910 may be adjusted according to variations in the physical dimensions of absorbent area 112. For example, absorbent article may be a diaper with different weight profiles and shaped absorbent areas. Therefore, there may be variations in the amount of hydration retained per unit length of the absorbent area. Spacings 1911 may be adjusted to account for the variations in the retained hydration along the length of ruler 1910.

Determining Hydration in a Person

As described earlier, determining whether a person is properly hydrated may involve determining a fluid output rate from the person. The total amount of fluid (hydration) output from a person may be computed, for example, using a hydration device 114 that indicates the volume of fluid received in an absorbent article worn by the person. Hydration device 114 may include, for example, the array resistor device, the spaced conductor device, wick based device, and a printed ruler described herein.

In addition to determining the total amount of fluid output from a person, the time period over which the hydration is received must also be determined to compute the fluid output rate. Referring back to FIG. 1, a timer 116 is provided to determine the time period over which hydration is received in the absorbent article.

In one embodiment of the invention timer 116 may be started at the time of first insult into the absorbent article. For example, timer 116 may include a temperature sensor to determine whether hydration is received in the absorbent article. If the temperature sensor detects a temperature greater than a threshold temperature value, timer 116 may be started. In one embodiment, timer 116 may be started in response to a change in an electrical property of the absorbent area. For example, timer 116 may be coupled with contacts disposed in the absorbent area. Hydration received in the absorbent area may electrically connect the contacts to one another, thereby starting the timer. In one embodiment, timer 116 may be started in response to a change in the equivalent resistance of the absorbent area.

Alternatively, timer 116 may be started at the time the absorbent article is worn by the person. For example, timer 116 may be manually started and/or stopped by pressing a button. In one embodiment, timer 116 may be electrically connected to contacts disposed in the absorbent article. The timer may be started when the contacts are brought into contact with each other, or the respective leads of a power source. In a particular embodiment, the contacts may be disposed on fasteners of the absorbent article, such that when the absorbent article (e.g. diaper) is placed on a user and fastened using the fasteners, the timer is initiated. In one embodiment, the timer may be started based on a fixed change in temperature of the absorbent article that may occur when a user wears the absorbent article.

In one embodiment, timer 118 may be permanently or temporarily locked to prevent resetting of the timer by a user of the absorbent article. For example, the timer may be coupled with a diaper for use by an infant or toddler. Therefore, timer 118 may be permanently or temporarily locked for preventing accidental reset of the timer by the user of the absorbent article. Any appropriate locking mechanism may be used. For example, in one embodiment, timer 118 may be reset only if a button associated with the timer is held down for a predefined period of time.

As previously described, timer 116 may be detachable from an absorbent article, thereby allowing reuse of timer 116 with multiple absorbent articles. Accordingly, the amount of hydration in each of the multiple absorbent articles may be determined using the techniques described earlier to compute a total amount of hydration output from the person. Timer 116 may provide a time period over which the total amount of hydration was received, thereby allowing a computation of the rate of fluid output from the person.

In one embodiment of the invention timer 116 may be communicably coupled with processing circuit 118. Processing circuit 118 may determine an amount of hydration received in the absorbent article using previously described techniques. Processing circuit 118 may also determine the fluid output rate for the person wearing the absorbent article.

In one embodiment, if processing circuit 118 determines that the fluid output rate is below an acceptable level, processing circuit 118 may alert a caregiver indicating that the person wearing the absorbent article is dehydrated. For example, processing circuit 118 may be configured to communicate with, for example, a computer, personal digital assistant (PDA), cell phone, or other similar electronic devices to alert a caregiver about hydration status.

In one embodiment, processing circuit 118 may be configured to communicate with an electronic record keeping device to provide such device data regarding the hydration status of a person. The record keeping device may store historical data regarding hydration of the person. The historical data stored in the record keeping device may be used to determine deviations from historical trends while determining hydration of the person.

Figure 20:
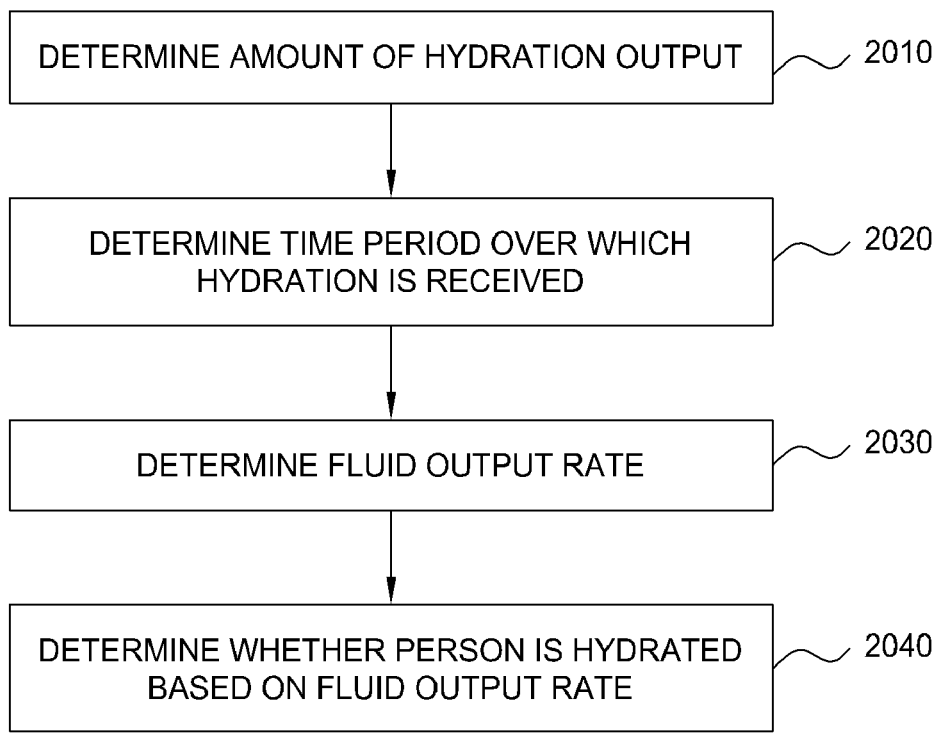
FIG. 20 is a flow diagram of exemplary operations performed to determine hydration of a person according to an embodiment of the invention.

FIG. 20 is a flow diagram of exemplary operations performed to determine hydration in a person. The operations begin in step 2010 by determining an amount of hydration output from the person. Determining the amount of hydration output from the person may involve determining an amount of hydration in an absorbent article. The amount of hydration in the absorbent article may be indicated by an alteration of a physical or electrical property of a device in the absorbent article.

In step 2020, the time period over which the hydration is received may be determined. For example, a timer 116 may be started at the time of a first insult into an absorbent article. Timer 116 may track the time period over which hydration is received in the absorbent article or multiple absorbent articles.

In step 2030, a fluid output rate may be computed based on the amount of hydration output by the person and the time period over which hydration was received. In step 2040, the hydration of the person may be determined based on the fluid output rate. For example, if the fluid output rate is below a threshold level, the person may be deemed to be dehydrated.

One skilled in the art will recognize that embodiments of the invention are not limited to determining the hydration of a person. Embodiments of the invention are generally adapted to determine a fluid output rate based on hydration received in an absorbent article. For example, in some embodiments, a rate of bleeding into a bandage may be determined. The rate of bleeding into the bandage may prove to be significant in the treatment of the person.

Furthermore, embodiments of the invention are not limited to use on persons. Embodiments of the invention may be incorporated into products for measuring a fluid output rate from any living entity, for example, animals and plants, and even non living entities, for example, to determine the fluid output rate from a leaking pipe.

CONCLUSION

By allowing a more accurate estimation of the amount of hydration in an absorbent article worn by a person, embodiments of the invention allow a more precise determination of a fluid output rate from the person, thereby allowing a determination of the hydration level in the person. Such determination may be critical to caregivers such as mothers of newborns and caregivers to elderly and the disabled to ensure proper nutrition and health of the person.

While the foregoing is directed to embodiments of the present invention, other and further embodiments of the invention may be devised without departing from the basic scope thereof, and the scope thereof is determined by the claims that follow.

What is claimed is:

1. An absorbent article comprising:
a device for measuring an amount of hydration in the absorbent article, the device being disposed in an absorbent area for receiving hydration in the absorbent article, wherein the hydration alters at least one of an electrical property and a physical property of the device, the altering of the property providing an indication of a plurality of degrees of an amount of hydration in the absorbent article irrespective of the number of times the absorbent article is insulted, wherein the device comprises a plurality of resistors wherein the hydration connects one or more resistors of the plurality of resistors to each other, thereby altering an equivalent resistance of the device, the equivalent resistance indicating the amount of hydration, and wherein the equivalent resistance correlates to a dimension of one or more insult areas of the absorbent article, the one or more insult areas defined by the hydration, wherein the dimension correlates to the amount of hydration;
a timer for determining a time period over which hydration is received in the absorbent article;
an output device including a receiver for receiving a recommended course of action from a peripheral device, wherein the output device is configured to display the received recommended course of action; and
a processing circuit configured to receive one or more inputs from a caregiver and to provide the output device data associated with the hydration of the absorbent article.

2. The absorbent article of claim 1, wherein the device comprises a ruler printed with ink on the absorbent area, wherein the hydration alters a visual characteristic of the ink in a hydrated area defined by the hydration, whereby a length of the ruler comprising the altered ink provides an indication of the amount of hydration.

3. The absorbent article of claim 1, wherein the device comprises a first conductor and a second conductor disposed separate from one another in the absorbent area, wherein the hydration electrically connects a portion of the first conductor to a portion of the second conductor thereby altering a resistance between the first conductor and the second conductor, the resistance indicating the amount of hydration.

4. The absorbent article of claim 3, wherein the first conductor is made from a material different than a material of the second conductor.

5. The absorbent article of claim 3, wherein the first conductor has a surface area different than the surface area of the second conductor.

6. The absorbent article of claim 3, wherein the first conductor comprises a pattern of conductive ink configured to increase a resolution of resistance along a surface of the first conductor.

7. The absorbent article of claim 1, wherein the device comprises a wick, wherein the hydration hydrates a portion of the wick, thereby altering a resistance of the wick, the equivalent resistance indicating an amount of hydration.

8. The absorbent article of claim 7, wherein a rate of the hydration of the wick provides an indication of a number of insults in the product and an amount of hydration.

9. The absorbent article of claim 7, wherein the wick comprises a material of a first conductivity value and a plurality of zones defined in the wick, the zones having a second conductivity value, wherein the zones increase a resolution of resistance change along the wick.

* * * * *